United States Patent
Hong et al.

(10) Patent No.: US 12,252,508 B2
(45) Date of Patent: *Mar. 18, 2025

(54) GINSENOSIDE AND ANTI-INFLAMMATORY COMPOSITION COMPRISING SAME

(71) Applicant: AMOREPACIFIC CORPORATION, Seoul (KR)

(72) Inventors: Yong Deog Hong, Yongin-si (KR); Hyun Woo Jeong, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 957 days.

This patent is subject to a terminal disclaimer.

(21) Appl. No.: 17/267,666

(22) PCT Filed: Jun. 27, 2019

(86) PCT No.: PCT/KR2019/007815
§ 371 (c)(1),
(2) Date: Feb. 10, 2021

(87) PCT Pub. No.: WO2020/036308
PCT Pub. Date: Feb. 20, 2020

(65) Prior Publication Data
US 2021/0309693 A1  Oct. 7, 2021

(30) Foreign Application Priority Data

Aug. 13, 2018 (KR) .................. 10-2018-0094381
Jun. 3, 2019 (KR) .................. 10-2019-0065376

(51) Int. Cl.
*C07J 17/00* (2006.01)
*A23L 33/105* (2016.01)
(Continued)

(52) U.S. Cl.
CPC ............ *C07J 17/005* (2013.01); *A23L 33/105* (2016.08); *A61K 8/63* (2013.01); *A61K 9/0014* (2013.01);
(Continued)

(58) Field of Classification Search
CPC ...... A61K 8/63; A61K 8/602; A61K 31/7048; A61K 31/704; A61P 29/00; A61Q 19/00; C07H 15/256
(Continued)

(56) References Cited

U.S. PATENT DOCUMENTS 10,722,442 B2 *  7/2020  Hong .................. A61Q 19/02
11,000,537 B2 *  5/2021  Hong .................. A61K 31/7048
(Continued)

FOREIGN PATENT DOCUMENTS

CN  102010456 B  7/2012
CN  102875628 A  1/2013
(Continued)

OTHER PUBLICATIONS

Rho et al Journal of Ginseng Research, 2020, 44, 145-153.*
(Continued)

*Primary Examiner* — Eric Olson
(74) *Attorney, Agent, or Firm* — Merchant & Gould P.C.

(57) ABSTRACT

The present specification relates to (20S,24R)-6-O-β-D-glucopyranosyl(1→2)-β-D-glucopyranoside-dammar-3-one-20,24-epoxy-6a,12b,25-triol, which is a novel ginsenoside, a pharmaceutically acceptable salt thereof, a hydrate thereof or a solvate thereof. The novel ginsenoside exhibits excellent anti-inflammatory effects.

8 Claims, 36 Drawing Sheets

(51) Int. Cl.
 *A61K 8/63* (2006.01)
 *A61K 9/00* (2006.01)
 *A61K 31/704* (2006.01)
 *A61Q 19/00* (2006.01)
 *C07H 15/256* (2006.01)
(52) U.S. Cl.
 CPC ............ *A61K 31/704* (2013.01); *A61Q 19/00* (2013.01); *C07H 15/256* (2013.01); *A61K 2800/74* (2013.01)
(58) Field of Classification Search
 USPC .......................................................... 514/26
 See application file for complete search history.

(56) References Cited

U.S. PATENT DOCUMENTS

| 11,000,538 | B2* | 5/2021 | Hong | .................. | A61K 9/0029 |
| 11,576,923 | B2* | 2/2023 | Hong | .................. | A61K 36/258 |
| 11,633,413 | B2* | 4/2023 | Hong | .................. | A61K 36/258 514/53 |

FOREIGN PATENT DOCUMENTS

| CN | 102924556 A | 2/2013 |
| CN | 103193848 A | 7/2013 |
| JP | 2001-139483 A | 5/2001 |
| KR | 1996-0040368 A | 12/1996 |
| KR | 10-0178867 B1 | 3/1999 |
| KR | 10-1457621 B1 | 7/2012 |
| KR | 10-1312389 B1 | 9/2013 |
| KR | 10-2014-0047645 A | 4/2014 |
| KR | 10-1445303 B1 | 9/2014 |
| KR | 10-2015-0055145 A | 5/2015 |
| KR | 10-1568658 B1 | 11/2015 |
| KR | 10-2016-0086149 A | 7/2016 |
| KR | 10-2016-0109189 A | 9/2016 |
| KR | 10-2017-0059549 A | 5/2017 |
| KR | 10-2018-0081660 A | 7/2018 |
| WO | 2005/000245 A2 | 1/2005 |
| WO | 2005/000248 A2 | 1/2005 |
| WO | 2005/040189 A1 | 5/2005 |

OTHER PUBLICATIONS

Dinh et al, Biomed Research International, 2014, pp. 1-11.*
Kim et al., "Sterols isolated from seeds of Panax ginseng and their antiinflammatory activities" Pharmacognosy Magazine vol. 9 issue 34 pp. 182-185, DOI: 10.4103/0973-1296.111288 (Year: 2013).*
Jin-Ping Liu et al., "Two novel dammarane-type compounds from the leaves and stems of Panax quinquefolium L.", Journal of Asian Natural Products Research, vol. 15, No. 9: 974-978 (2013).
Seiji Fujita et al., "Dammarane Glycosides From Aerial Part of Neoalsomitra Integrifoliola", Phytochemistry, vol. 39, No. 3: 591-602 (1995).
Taewoong Rho et al., "Identification of a novel triterpene saponin from Panax ginseng seeds, pseudoginsenoside RT8, and its antiinflammatory activity", Journal of Ginseng Research, Available online Nov. 10, 2018.
Yang Jie et al., "Semisynthesis and Cytotoxicity Evaluation of a Series of Ocotillol Type Saponins and Aglycones from 20(S)-Ginsenoside Rg2, Rh1, Protopanaxatriol and Their 20(R)-Epimers", Chem. Res. Chin. Univ., vol. 32, No. 1: 35-40 (2016).
Osamu Tanaka et al., "Study on Saponins of Rhizomes of *Panax pseudo-ginseng* subsp. himalaicus Collected at Tzatogang and Pari-la, Bhutan-Himalaya", Chem. Pharm. Bull., vol. 33, No. 6: 2323-2330 (1985).
CAS RN : 2170771-84-1 (The capture image file of the STN International Database) Dated Jun. 2, 2020.
CAS RN : 2170771-84-1 (The capture image file of the STN International Database) Dated Jul. 2, 2019.
International Search Report PCT/KR2019/007815, dated Oct. 1, 2019.

* cited by examiner

1: R₁ = Glc; R₂ = H
2: R₁ = H; R₂ = Rha
3: R₁ = Glc; R₂ = Rha

4: $R_1$ = Glc; $R_2$ = H
5: $R_1$ = Glc; $R_2$ = Glc
6: $R_1$ = Glc; $R_2$ = Ara

7: R = Glc

8: R = Glc

9: R = Glc

10

11

12

13

14

15

16

Chemical Formula: $C_{42}H_{72}O_{14}$
Exact Mass: 800.4922

1. Ginsenoside Rg1

Chemical Formula: $C_{42}H_{72}O_{13}$
Exact Mass: 784.4973

2. (20S)-Ginsenoside Rg2

Chemical Formula: $C_{48}H_{82}O_{18}$
Exact Mass: 946.5501

3. Ginsenoside Re

Chemical Formula: $C_{48}H_{82}O_{18}$
Exact Mass: 946.5501

4. Ginsenoside Rd

Chemical Formula: $C_{54}H_{92}O_{23}$
Exact Mass: 1108.6029

5. Ginsenoside Rb1

Chemical Formula: $C_{53}H_{90}O_{22}$
Exact Mass: 1078.5924

6. Ginsenoside Rb2

GINSENOSIDE AND ANTI-INFLAMMATORY COMPOSITION COMPRISING SAME

CROSS-REFERENCE TO RELATED APPLICATIONS

This application is a National Stage Application of PCT/KR2019/007815, filed Jun. 27, 2019, which claims benefit of priority to Serial No. 10-2018-0094381, filed Aug. 13, 2018 and Serial No. 10-2019-0065376, filed Jun. 3, 2019 in the Republic of Korea and which applications are incorporated herein by reference. To the extent appropriate, a claim of priority is made to each of the above disclosed applications.

TECHNICAL FIELD

The present disclosure relates to a novel ginsenoside.

BACKGROUND ART

*Ginseng* (*Panax ginseng* C.A. Meyer) is a plant belonging to the genus *Panax* of the family Araliaceae. It has been used as an herb in folk medicine from about 2,000 years ago in Korea, China, Japan, etc. It is known that the representative physiologically active ingredients of ginseng are saponins, polysaccharides, peptides, sitosterols, polyacetylenes and fatty acids. Among them, the saponins of ginseng are called ginsenosides. The efficacies and effects of ginseng comprise activity on the central nervous system, anti-carcinogenic and anticancer activities, immunoregulatory activity, antidiabetic activity, liver function-enhancing efficacy, cardiovascular disease-improving and anti-arteriosclerotic activities, blood pressure-controlling activity, menopausal disorder- and osteoporosis-improving effects, anti-stress and anti-fatigue effects, antioxidant activity, antiaging effect, etc. Although the ginsenosides vary greatly in contents and compositions depending on the part of ginseng, such as root, leaf, fruit, flower, seed, etc., most of the known effects described above are those from the ginseng root, i.e., the root part of ginseng, and other parts of ginseng except the ginseng root have not been studied a lot.

Inflammation is a complex immune response for defending a living organism from harmful stimuli such as mechanical injuries, pathogens or irritants. When an inflammatory process is initiated by such inflammation-inducing factors, stimulated inflammatory cells express inflammatory mediators comprising pro-inflammatory cytokines such as interleukin (IL)-1$\beta$, IL-6 and tumor necrosis factor (TNF)-$\alpha$, nitric oxide (NO) and inducible nitric oxide synthase (iNOS) at higher levels for regulation of the cellular and tissue functions. However, abnormal regulation of inflammatory responses may also be triggered by non-pathogenic means. For example, free fatty acids may induce pro-inflammatory responses by binding to toll-like receptor 4. Low-grade chronic inflammation is associated with the onset of various metabolic disorders such as atherosclerosis, cancer, fatty liver disease, insulin resistance, rheumatoid arthritis, type 2 diabetes and vascular diseases. Therefore, in order to stay healthy, it is important to maintain the well-balanced inflammatory state.

REFERENCES OF RELATED ART

Patent Documents

Korean Patent Publication No. 10-2016-0086149.

DISCLOSURE

Technical Problem

In an aspect, the present disclosure is directed to providing a novel ginsenoside having superior anti-inflammatory effect and a composition comprising the same.

Technical Solution

In an aspect, the present disclosure provides (20S,24R)-6-O-$\beta$-D-glucopyranosyl(1→2)-$\beta$-D-glucopyranoside-dammar-3-one-20,24-epoxy-6a,12b,25-triol, a pharmaceutically acceptable salt thereof, a hydrate thereof or a solvate thereof.

In an aspect, the present disclosure provides an anti-inflammatory composition comprising (20S,24R)-6-O-$\beta$-D-glucopyranosyl(1→2)-$\beta$-D-glucopyranoside-dammar-3-one-20,24-epoxy-6a,12b,25-triol, a pharmaceutically acceptable salt thereof, a hydrate thereof or a solvate thereof as an active ingredient.

In another aspect, the present disclosure provides a use of (20S,24R)-6-O-$\beta$-D-glucopyranosyl(1→2)-$\beta$-D-glucopyranoside-dammar-3-one-20,24-epoxy-6a,12b,25-triol, a pharmaceutically acceptable salt thereof, a hydrate thereof or a solvate thereof for preparation of an anti-inflammatory composition.

In another aspect, the present disclosure provides an anti-inflammatory method comprising administering an effective amount of (20S,24R)-6-O-$\beta$-D-glucopyranosyl(1→2)-$\beta$-D-glucopyranoside-dammar-3-one-20,24-epoxy-6a,12b,25-triol, a pharmaceutically acceptable salt thereof, a hydrate thereof or a solvate thereof to a subject.

In another aspect, the present disclosure provides (20S,24R)-6-O-$\beta$-D-glucopyranosyl(1→2)-$\beta$-D-glucopyranoside-dammar-3-one-20,24-epoxy-6a,12b,25-triol, a pharmaceutically acceptable salt thereof, a hydrate thereof or a solvate thereof for use as an active ingredient in an anti-inflammatory composition. In addition, the present disclosure provides a non-therapeutic cosmetic use of (20S,24R)-6-O-$\beta$-D-glucopyranosyl(1→2)-$\beta$-D-glucopyranoside-dammar-3-one-20,24-epoxy-6a,12b,25-triol, a pharmaceutically acceptable salt thereof, a hydrate thereof or a solvate thereof as an active ingredient for anti-inflammation.

Advantageous Effects

In an aspect, the present disclosure may provide a novel ginsenoside having superior anti-inflammatory effect, a pharmaceutically acceptable salt thereof, a hydrate thereof or a solvate thereof, and a composition comprising the same. The novel ginsenoside exhibits remarkably superior anti-inflammatory effect as compared to the existing ginsenosides known to have anti-inflammatory effect.

BEST MODE

Figure 1:
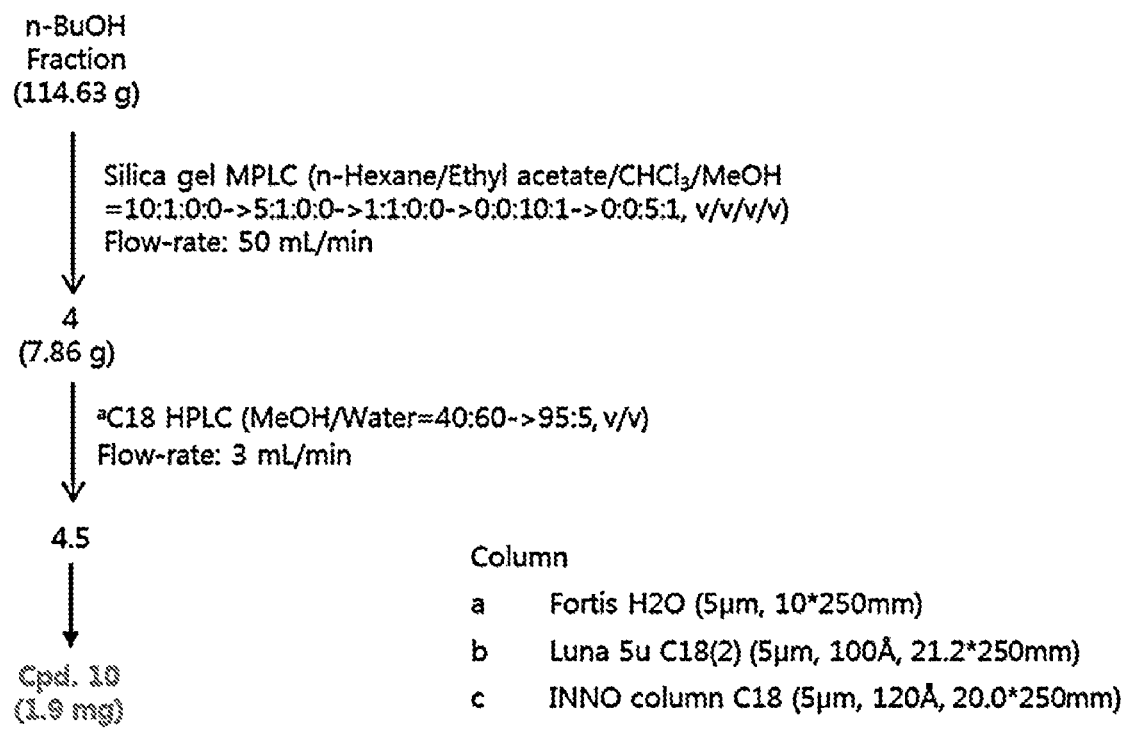
FIG. 1 shows a process of isolating a novel ginsenoside of the present disclosure (Cpd. 10) from among the compounds fractionated from a ginseng seed extract.
Figure 2A:
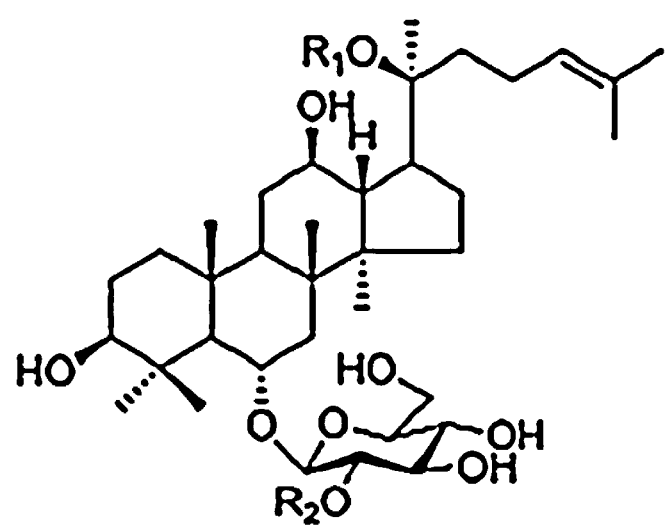
FIG. 2A shows the chemical structure of Compounds 1-3 fractionated from a ginseng seed extract.
Figure 2B:
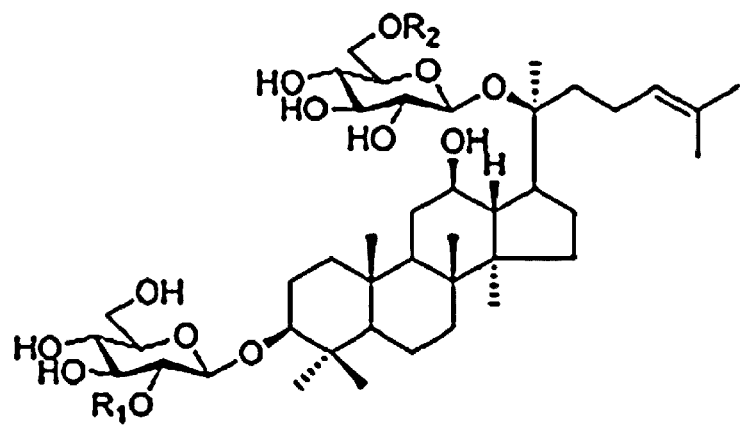
FIG. 2B shows the chemical structure of Compounds 4-6 fractionated from a ginseng seed extract.
Figure 2C:
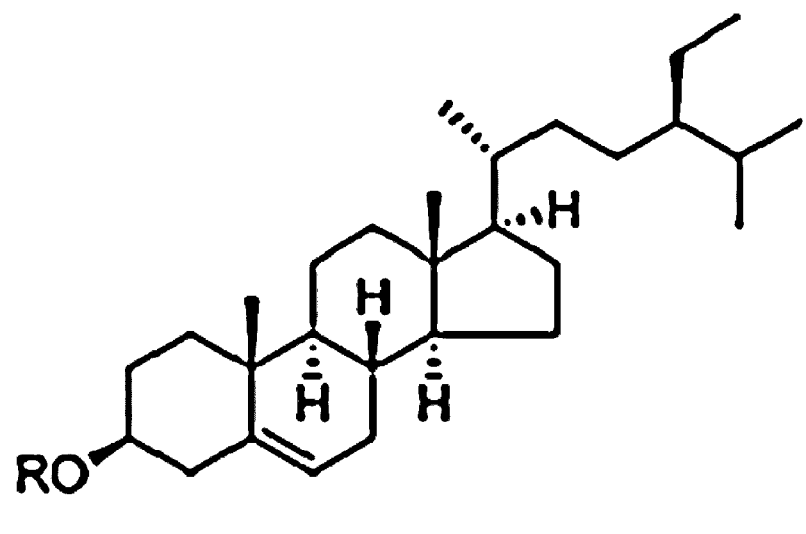
FIG. 2C shows the chemical structure of Compound 7 fractionated from a ginseng seed extract.
Figure 2D:
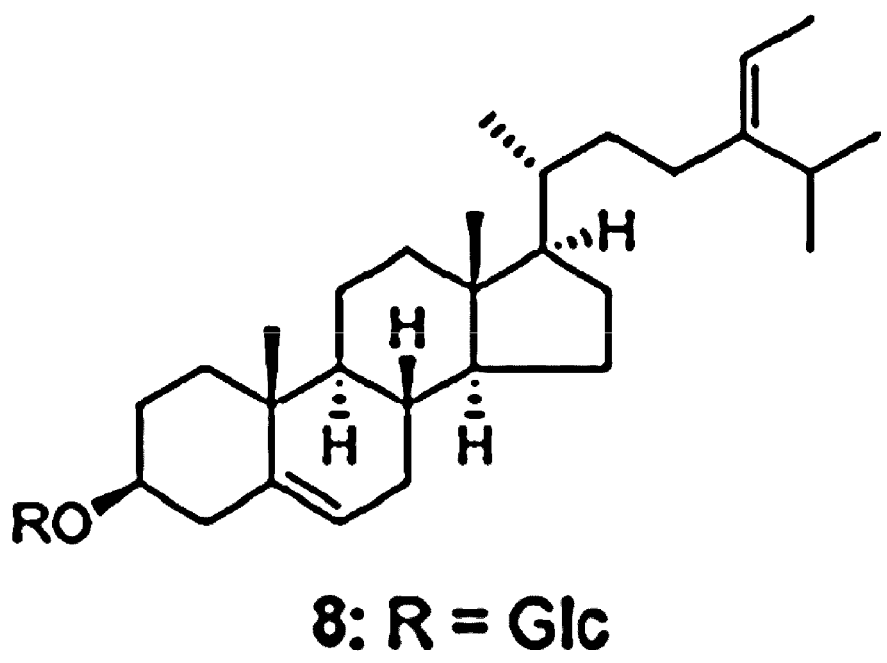
FIG. 2D shows the chemical structure of Compound 8 fractionated from a ginseng seed extract.
Figure 2E:
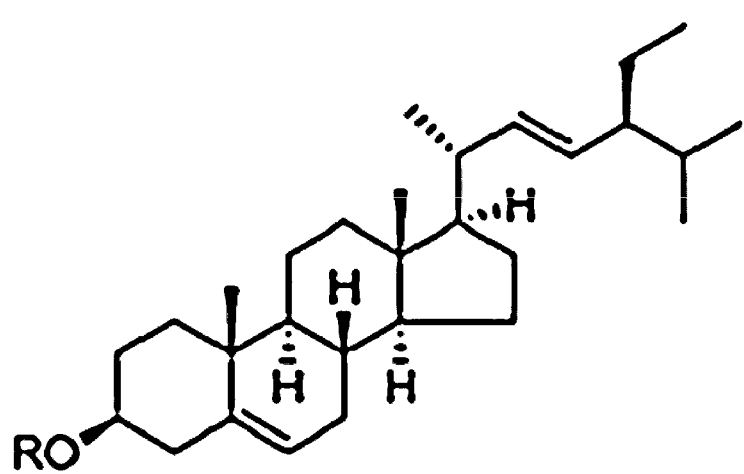
FIG. 2E shows the chemical structure of Compound 9 fractionated from a ginseng seed extract.
Figure 2F:
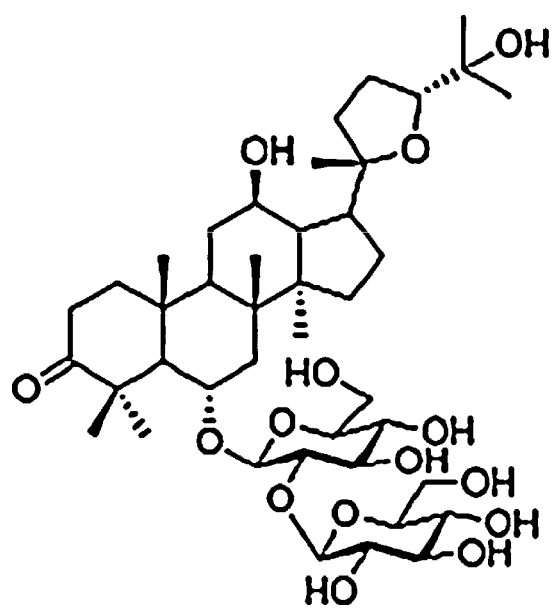
FIG. 2F shows the chemical structure of Compound 10 fractionated from a ginseng seed extract.
Figure 2G:
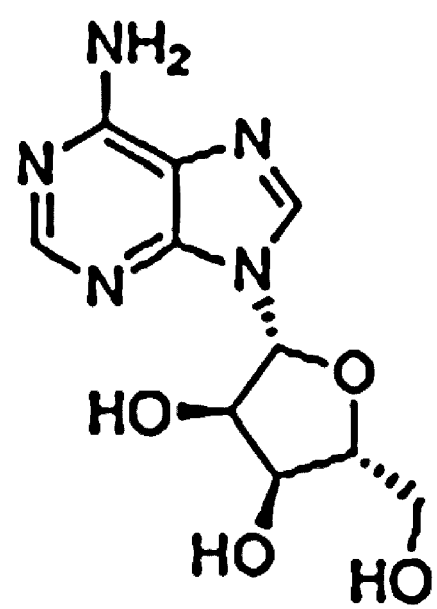
FIG. 2G shows the chemical structure of Compound 11 fractionated from a ginseng seed extract.
Figure 2H:
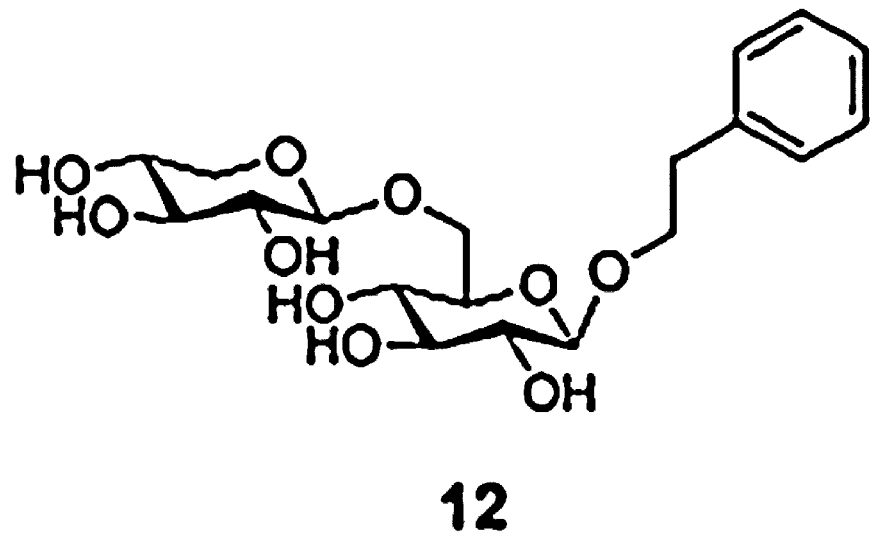
FIG. 2H shows the chemical structure of Compound 12 fractionated from a ginseng seed extract.
Figure 2I:
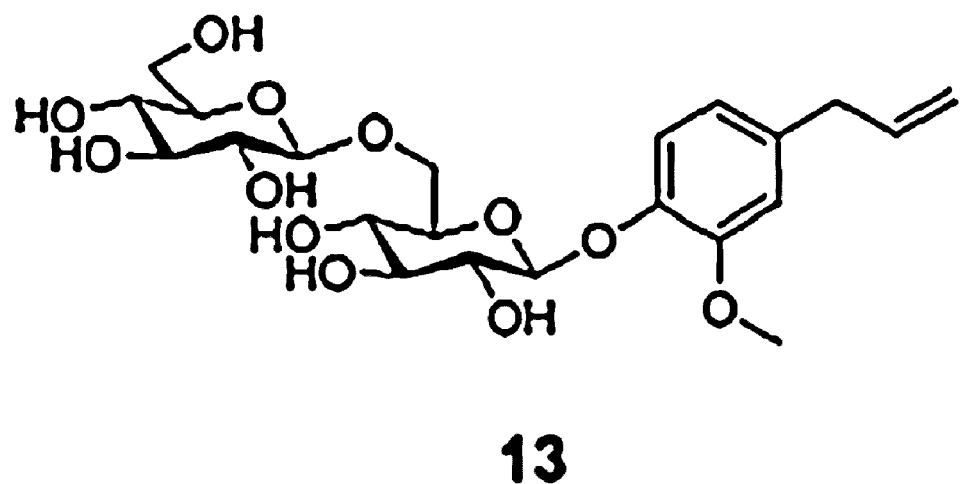
FIG. 2I shows the chemical structure of Compound 13 fractionated from a ginseng seed extract.
Figure 2J:
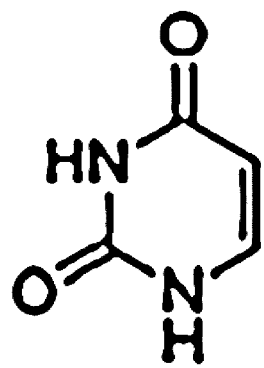
FIG. 2J shows the chemical structure of Compound 14 fractionated from a ginseng seed extract.
Figure 2K:
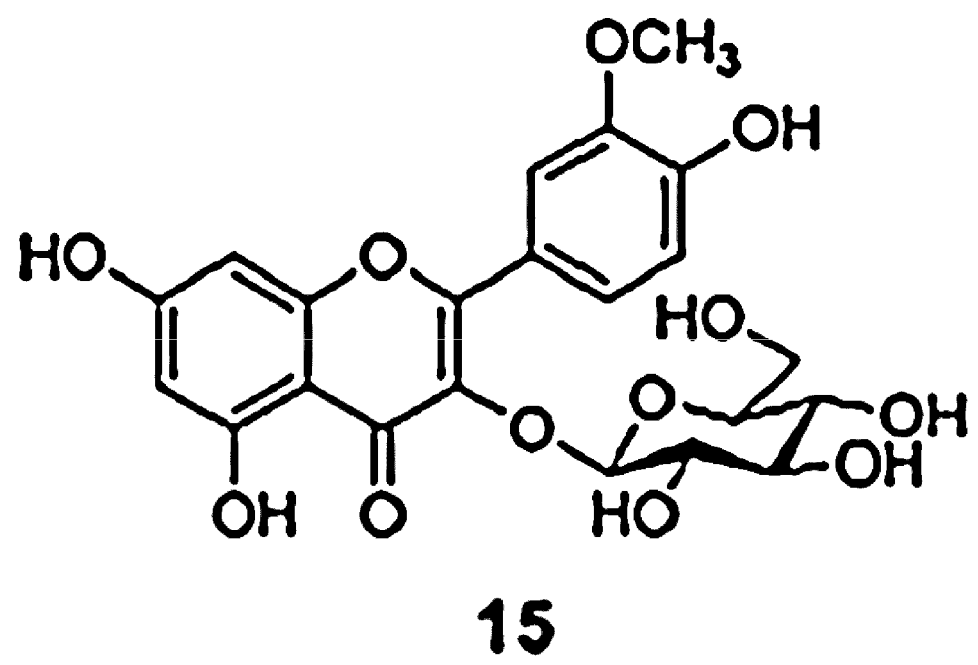
FIG. 2K shows the chemical structure of Compound 15 fractionated from a ginseng seed extract.
Figure 2L:
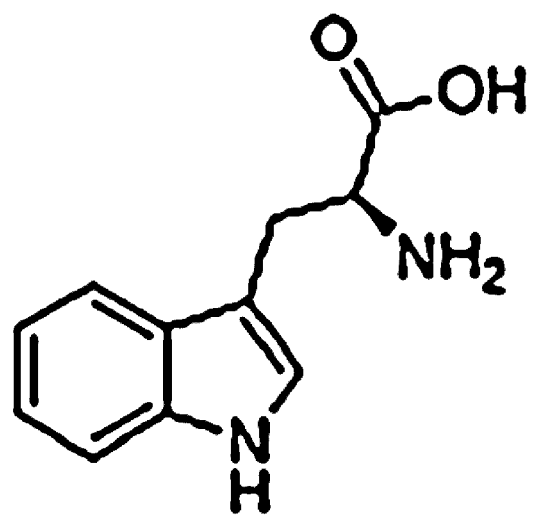
FIG. 2L shows the chemical structure of Compound 16 fractionated from a ginseng seed extract.
Figure 3A:
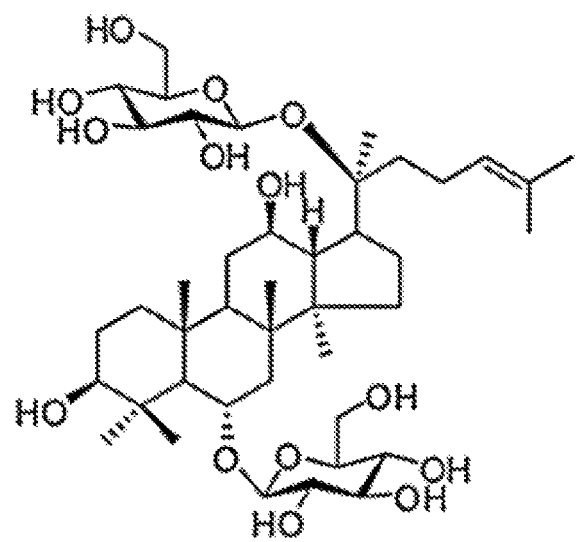
FIG. 3A shows the spectroscopic evidence and structure of Compound 1, which is a previously known ginsenoside fractionated from a ginseng seed extract.
Figure 3B:
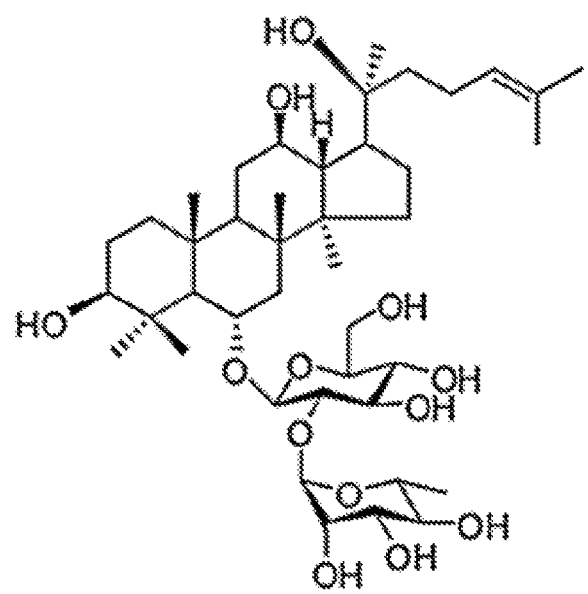
FIG. 3B shows the spectroscopic evidence and structure of Compound 2, which is a is previously known ginsenoside fractionated from a ginseng seed extract.
Figure 3C:
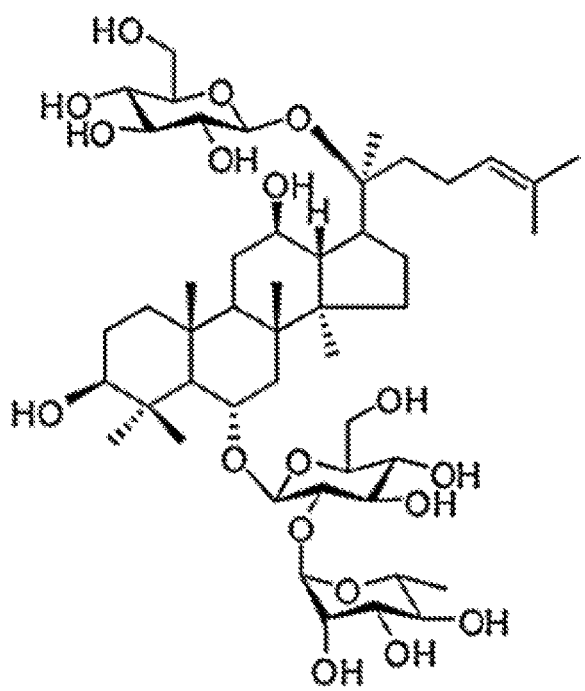
FIG. 3C shows the spectroscopic evidence and structure of Compound 3, which is a previously known ginsenoside fractionated from a ginseng seed extract.
Figure 3D:
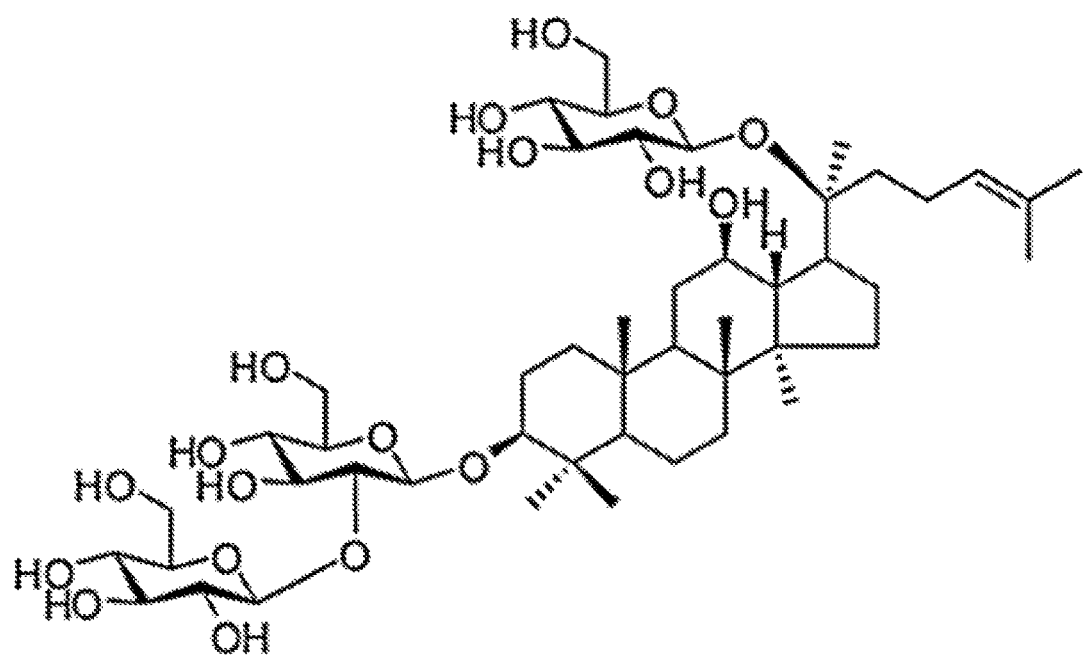
FIG. 3D shows the spectroscopic evidence and structure of Compound 4, which is a previously known ginsenoside fractionated from a ginseng seed extract.
Figure 3E:
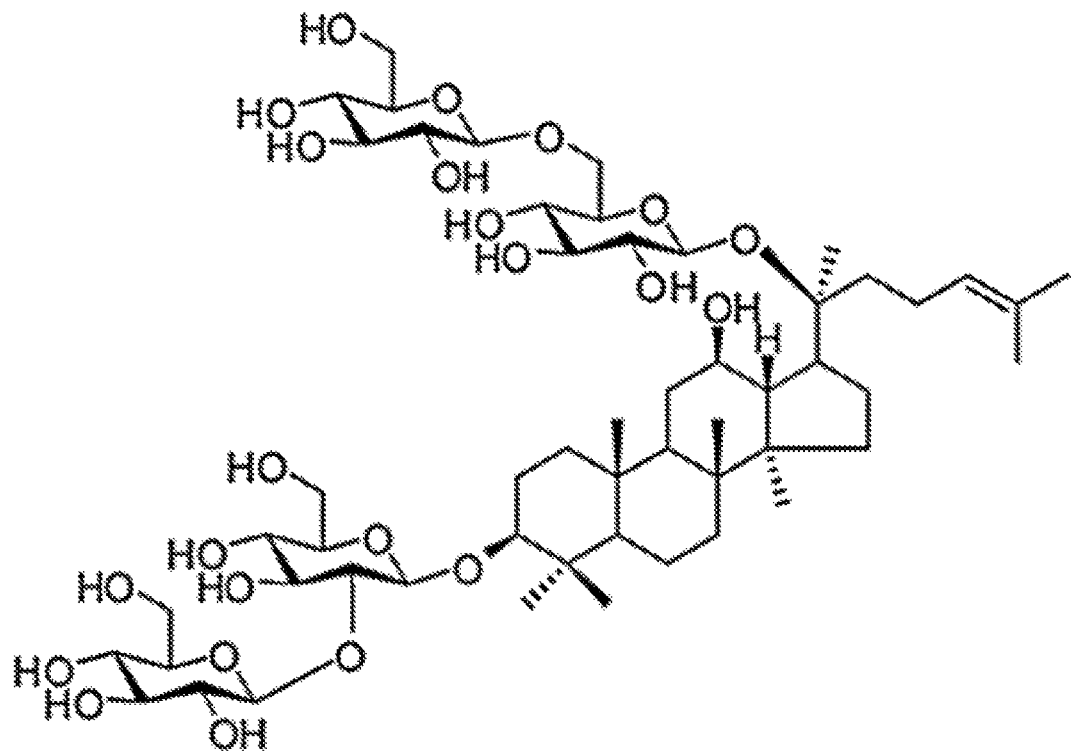
FIG. 3E shows the spectroscopic evidence and structure of Compound 5, which is a previously known ginsenoside fractionated from a ginseng seed extract.
Figure 3F:
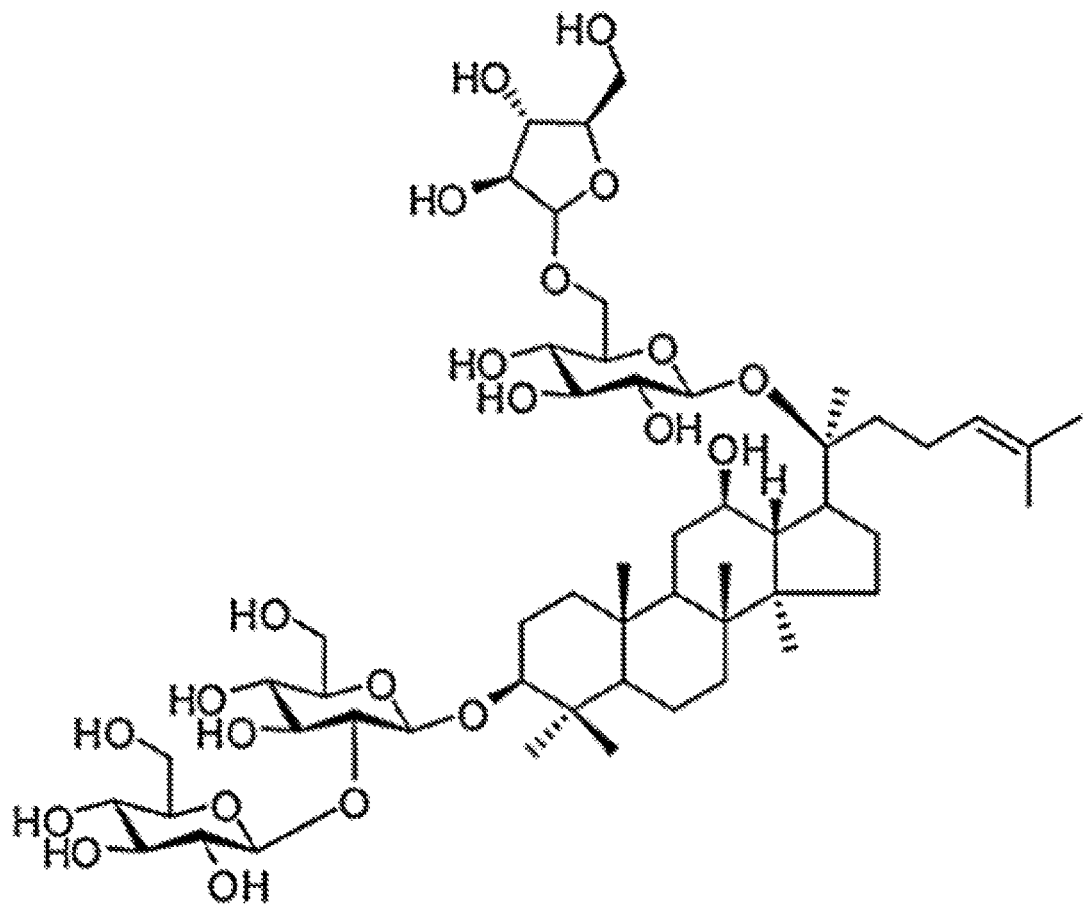
FIG. 3F shows the spectroscopic evidence and structure of Compound 6, which is a previously known ginsenoside fractionated from a ginseng seed extract.
Figure 4:
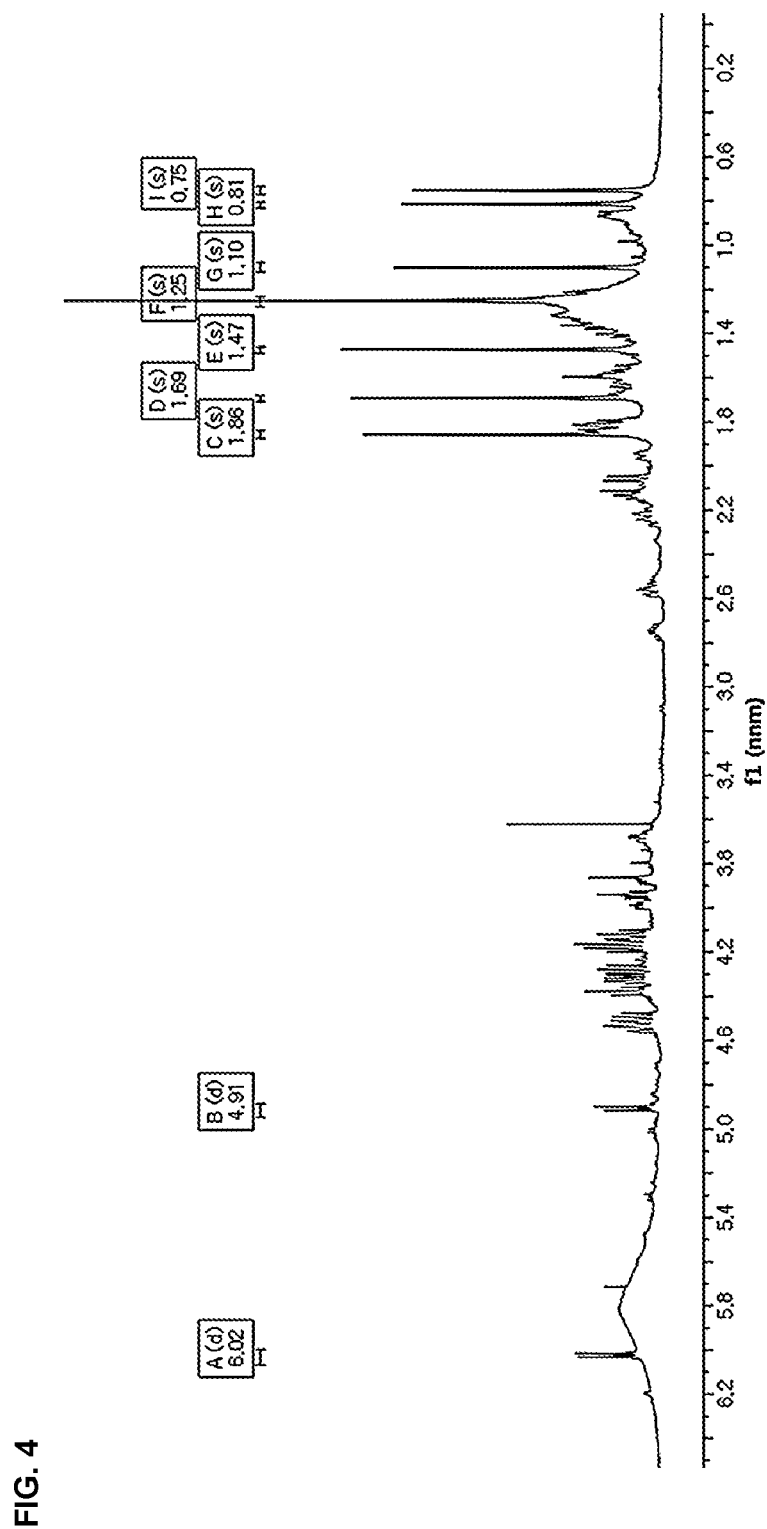
FIG. 4 shows the $^1$H-NMR spectrum of Compound 10, which is a novel ginsenoside of the present disclosure fractionated from a ginseng seed extract.
Figure 5:
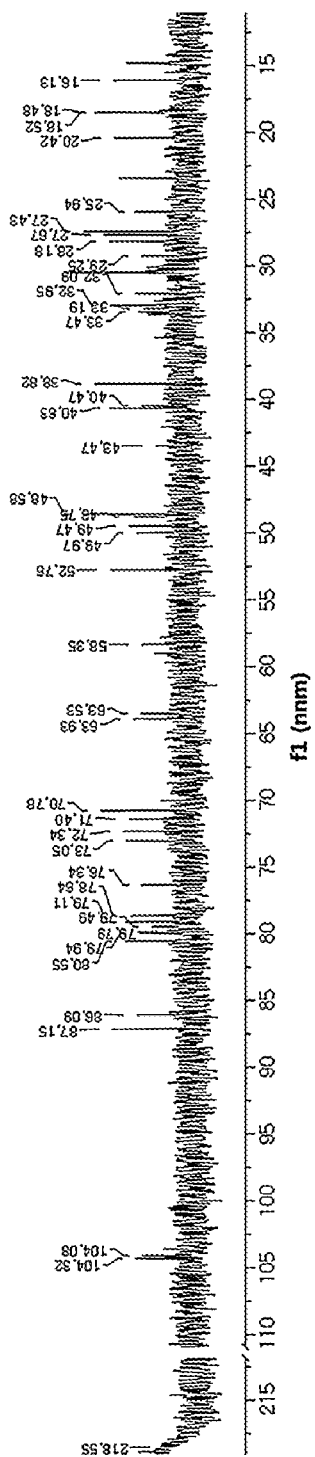
FIG. 5 shows the $^{13}$C-NMR spectrum of Compound 10, which is a novel ginsenoside of the present disclosure fractionated from a ginseng seed extract.
Figure 6:
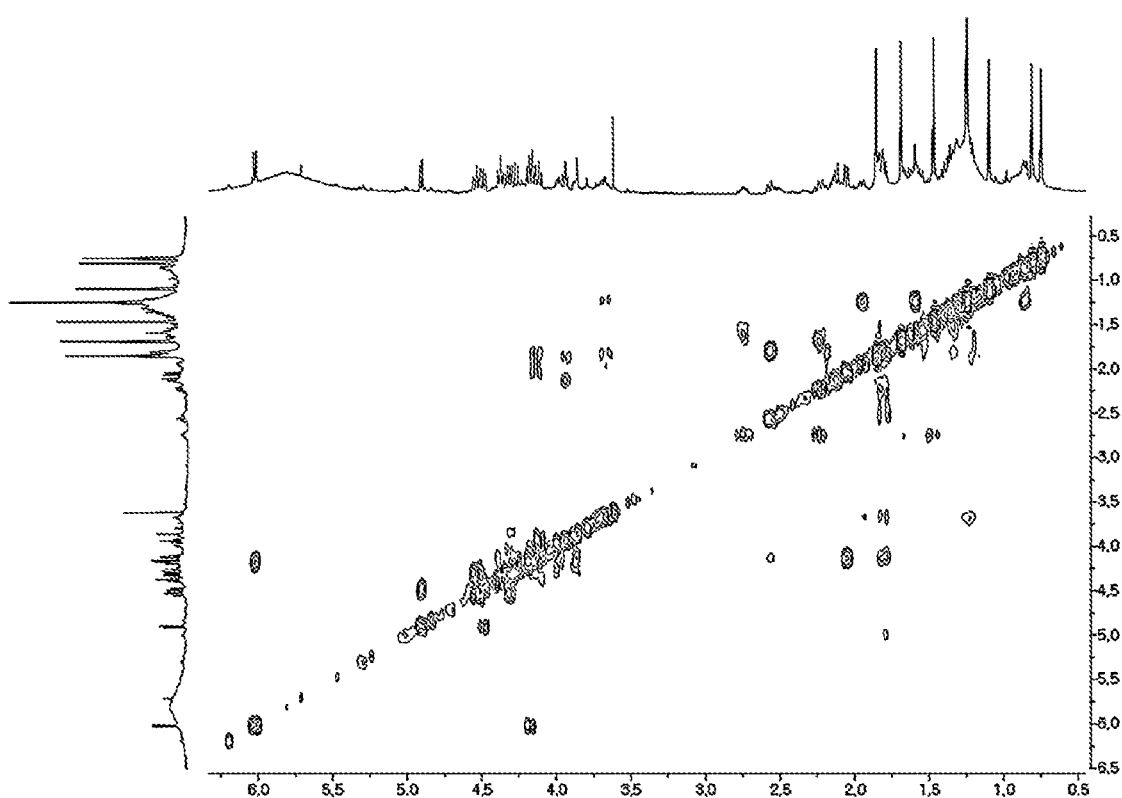
FIG. 6 shows the COSY spectrum of Compound 10, which is a novel ginsenoside of the present disclosure fractionated from a ginseng seed extract.
Figure 7:
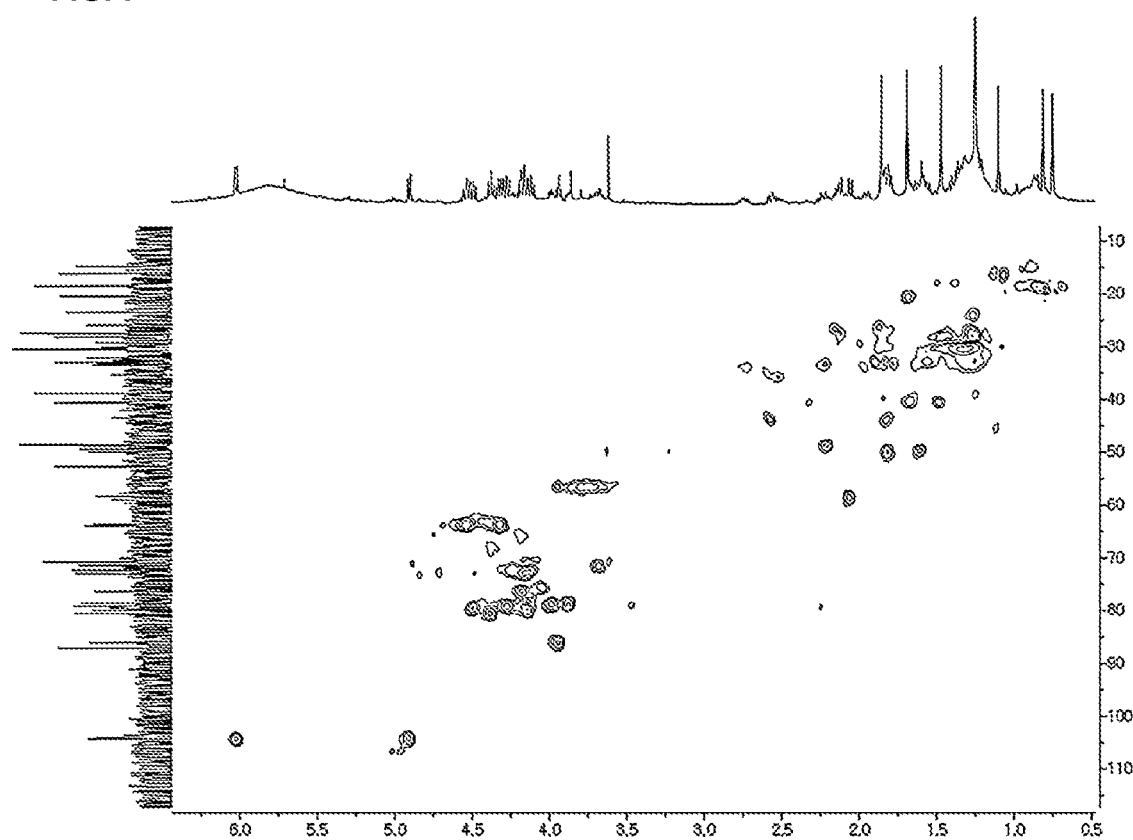
FIG. 7 shows the HSQC spectrum of Compound 10, which is a novel ginsenoside of the present disclosure fractionated from a ginseng seed extract.
Figure 8:
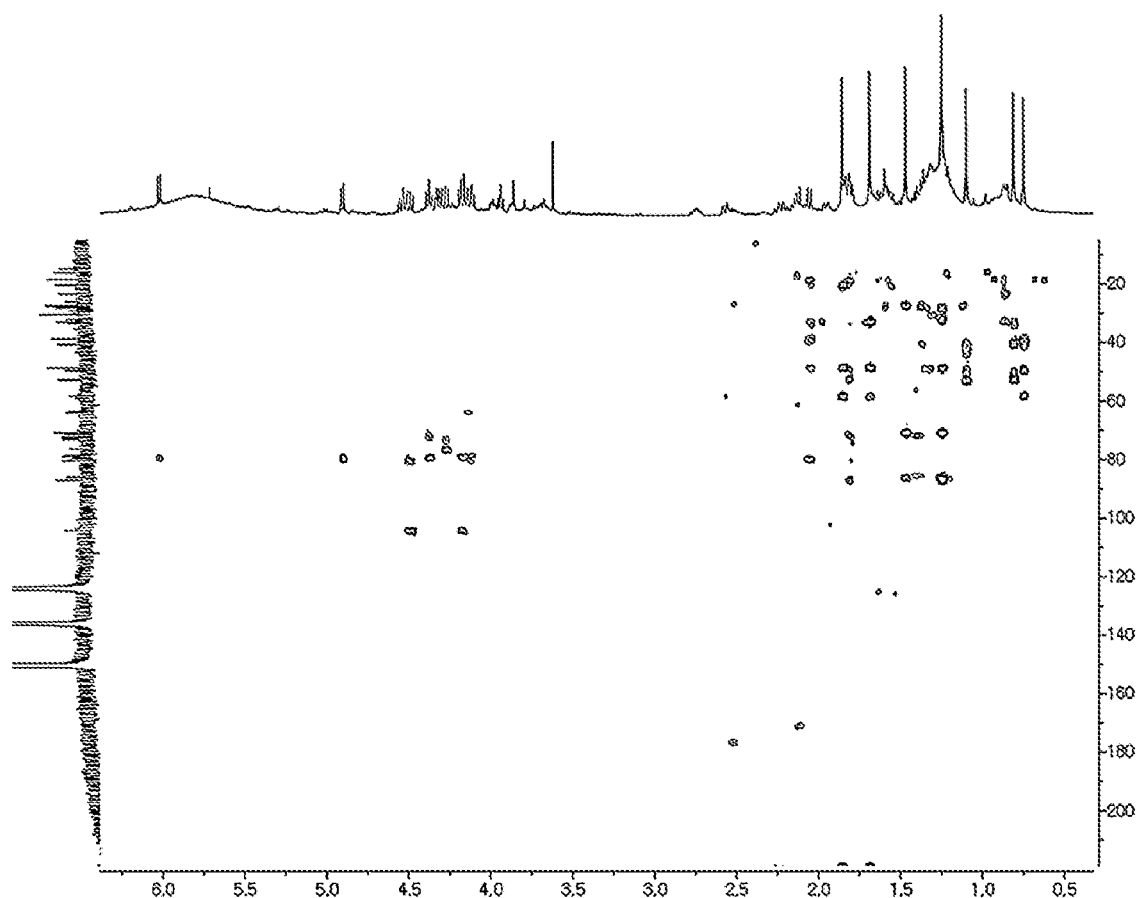
FIG. 8 shows the HMBC spectrum of Compound 10, which is a novel ginsenoside of the present disclosure fractionated from a ginseng seed extract.
Figure 9:
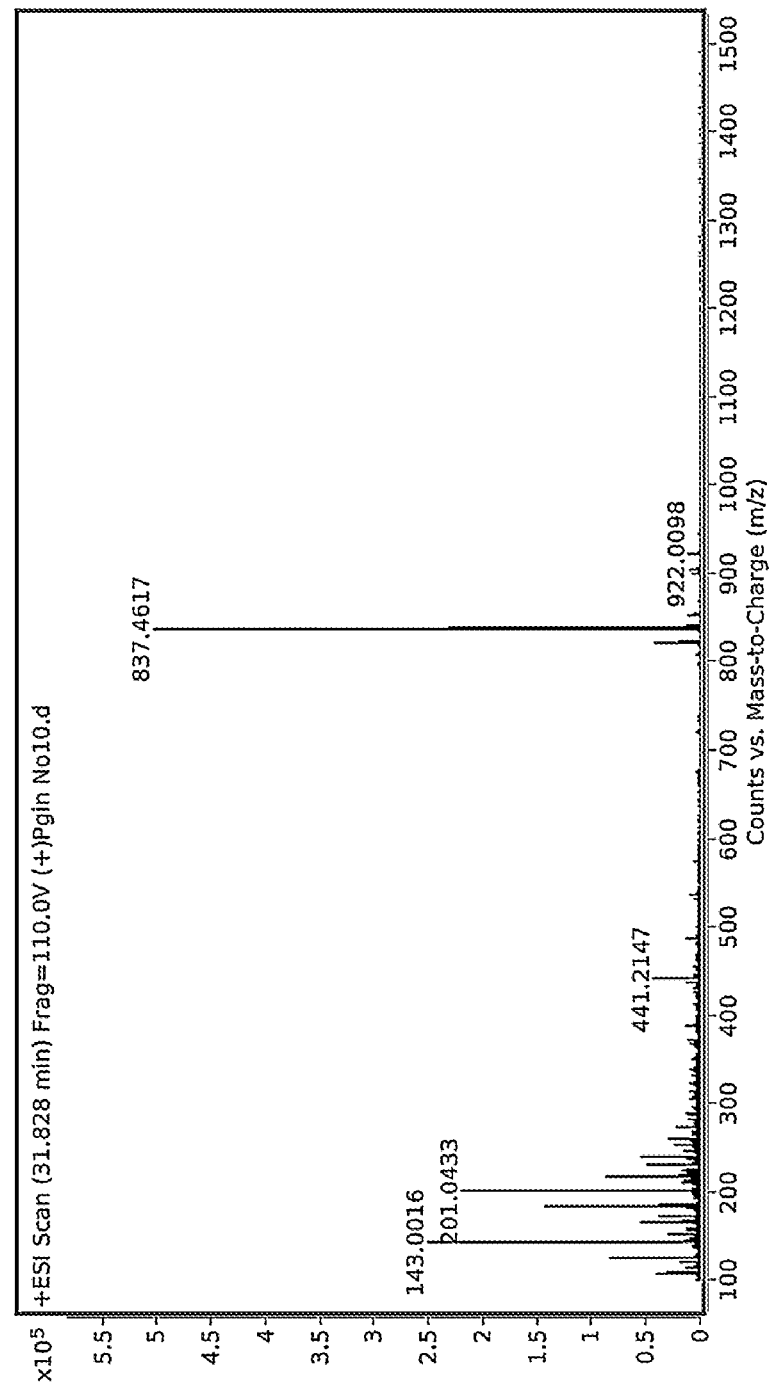
FIG. 9 shows the MS spectrum of Compound 10, which is a novel ginsenoside of the present disclosure fractionated from a ginseng seed extract.
Figure 10:
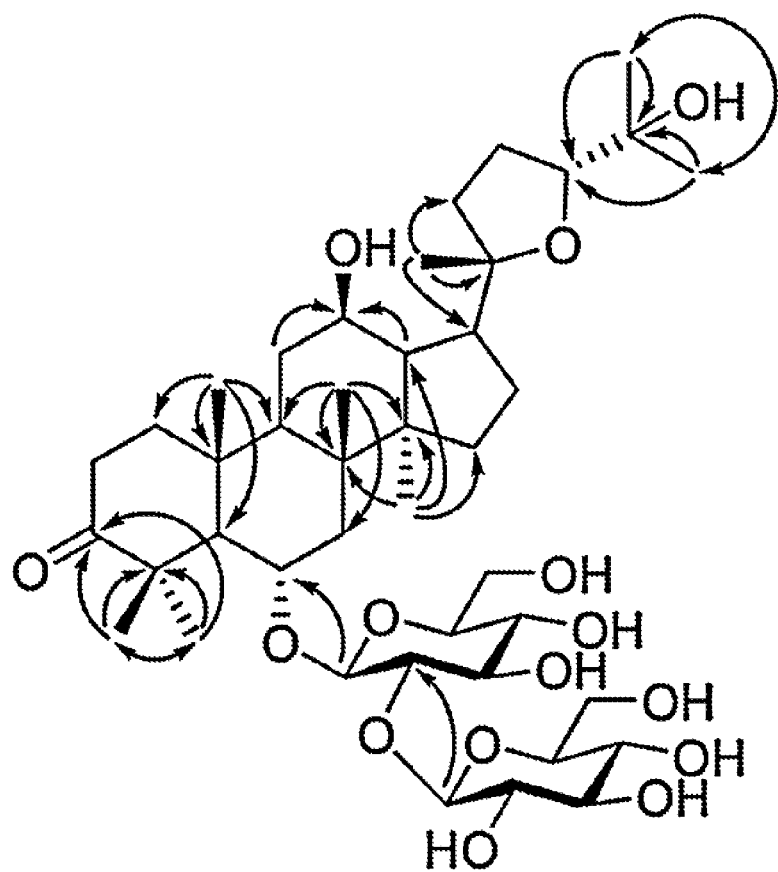
FIG. 10 shows the key HMBC correlation of Compound 10, which is a novel ginsenoside of the present disclosure fractionated from a ginseng seed extract.

Hereinafter, exemplary embodiments of the present disclosure will be described in more detail referring to the attached drawings. However, the present disclosure may be embodied in different forms without being limited to the exemplary embodiments described herein. Rather, the exemplary embodiments are provided so that this disclosure will be thorough and complete, and will fully convey the technical idea of the present disclosure to those skilled in the art. In the drawings, the sizes of some elements such as width, thickness, etc. are somewhat exaggerated in order to clarify the elements. In addition, although some elements are shown only in part for the convenience of explanation, those skilled in the art will easily understand the remaining part of the elements. In addition, those having ordinary knowledge in the art will be able to embody the technical idea of the present disclosure in various other forms without departing from the scope of the present disclosure.

In an exemplary embodiment, the present disclosure provides a novel ginsenoside (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof.

In an exemplary embodiment, the present disclosure may provide an anti-inflammatory composition comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof as an active ingredient.

In an exemplary embodiment, the present disclosure may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof for preparation of an anti-inflammatory composition.

In an exemplary embodiment, the present disclosure may provide an anti-inflammatory method comprising administering an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof to a subject.

In an exemplary embodiment, the present disclosure may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof as an active ingredient for use in an anti-inflammatory composition. In addition, the present disclosure may provide a non-therapeutic cosmetic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof as an active ingredient for anti-inflammation.

In the present disclosure, the term "pharmaceutically acceptable salt" refers to a salt according to one aspect of the present disclosure that is pharmaceutically acceptable and possesses the desired pharmacological activity of the parent compound. The salts comprise (1) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, or the like; or (2) salts formed when an acidic proton present in the parent compound is substituted.

In the present disclosure, a "hydrate" refers to a compound bound with water. It is used in a broad sense, comprising an inclusion compound which lacks chemical bonding with water.

In the present disclosure, a "solvate" refers to a higher-order compound formed between a solute molecule or ion and a solvent molecule or ion.

In an exemplary embodiment, the ginsenoside is a novel triterpene saponin having a molecular formula $C_{42}H_{70}O_{15}$ and having the following chemical structure.

Chemical Formula 1

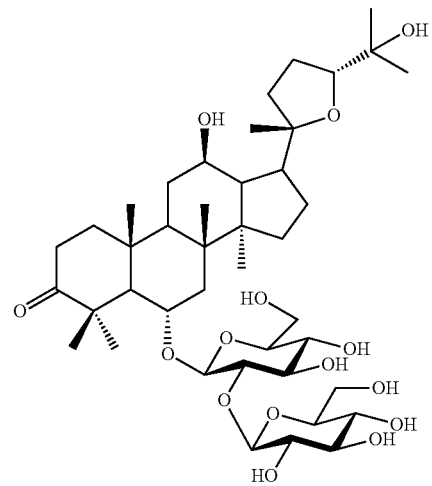

In the present disclosure, the novel ginsenoside is named "pseudoginsenoside $RT_8$" or "PG-$RT_8$".

In an exemplary embodiment, the ginsenoside may be one extracted from ginseng seed. More specifically, the ginsenoside may be one isolated from a ginseng seed extract, although not being limited thereto. In an exemplary embodiment, the ginseng seed may be the seed of *Panax ginseng* C.A. Meyer.

In the present disclosure, "isolation" means extraction or fractionation from a ginseng seed extract using water or an organic solvent by any method known to those skilled in the art. The fractionation may be performed after the extraction.

As used herein, the term "extract" means a substance obtained by extracting a component contained inside of a natural substance, regardless of the extracted method or ingredients. The term is used in a broad sense comprising, for example, all of those obtained by extracting a component soluble in a solvent from a natural substance using water or an organic solvent, extracting only a specific component of a natural substance, or the like.

In the present disclosure, the "fraction" comprises a fraction obtained by fractionating a specific substance or extract using a solvent, a remainder remaining after the fractionation, or a fraction obtained by extracting again using a specific solvent. The fractionation or extraction may be conducted by any methods known to those of ordinary skill in the art.

In an exemplary embodiment, the ginsenoside may be one isolated from a methanol- and butanol-soluble extract of ginseng seed. Specifically, the ginsenoside may be detected and isolated from a methanol- and butanol-soluble extract of ginseng seed by HPLC-ESI-Q-TOF-MS. Since the main components of the ginseng seed extract are lipids, not all triterpene and steroidal saponins can be observed from a crude extract of ginseng seed by HPLC-UV or HPLC-ELSD.

In an exemplary embodiment, the present disclosure may provide a composition inhibiting the expression of one or more gene of the pro-inflammatory genes interleukin 1β (IL-1β), interleukin 6 (IL-6) and inducible nitric oxide synthase (iNOS), which comprises the ginsenoside, a pharmaceutically acceptable salt thereof, a hydrate thereof or a solvate thereof. In an exemplary embodiment, the present disclosure may provide a composition inhibiting the production and secretion of inflammatory cytokines, which are inflammation-mediating signaling proteins, which comprises the ginsenoside, a pharmaceutically acceptable salt thereof, a hydrate thereof or a solvate thereof. In an exemplary embodiment, the present disclosure may provide a composition inhibiting the production of nitric oxide (NO), which is a mediator of inflammatory response, which comprises the ginsenoside, a pharmaceutically acceptable salt thereof, a hydrate thereof or a solvate thereof.

In an exemplary embodiment, the present disclosure may provide a composition having remarkably superior anti-inflammatory effect as compared to existing ginsenosides known to have anti-inflammatory effect.

In an exemplary embodiment, the active ingredient may be comprised in an amount of 0.0001-99.9 wt % based on the total weight of the composition. Specifically, in an exemplary embodiment, the composition may comprise the active ingredient in an amount of 0.0001 wt % or more, 0.0005 wt % or more, 0.001 wt % or more, 0.01 wt % or more, 0.1 wt % or more, 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 15 wt % or more, 20 wt % or more, 25 wt % or more, 30 wt % or more, 35 wt % or more, 40 wt % or more, 45 wt % or more, 50 wt % or more, 55 wt % or more, 60 wt % or more, 65 wt % or more, 70 wt % or more, 75 wt % or more, 80 wt % or more, 85 wt % or more, 90 wt % or more, 95 wt % or more or 99.9 wt % or more based on the total weight of the composition, although not being limited thereto. In addition, in an exemplary embodiment, the composition may comprise the active ingredient in an amount of 100 wt % or less, 99 wt % or less, 95 wt % or less, 90 wt % or less, 85 wt % or less, 80 wt % or less, 75 wt % or less, 70 wt % or less, 65 wt % or less, 60 wt % or less, 55 wt % or less, 50 wt % or less, 45 wt % or less, 40 wt % or less, 35 wt % or less, 30 wt % or less, 25 wt % or less, 20 wt % or less, 15 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.5 wt % or less, 0.1 wt % or less, 0.01 wt % or less, 0.001 wt % or less or 0.0005 wt % or less based on the total weight of the composition, although not being limited thereto.

The composition according to an exemplary embodiment of the present disclosure may be composition for external application to skin, which comprises the active ingredient.

In the present disclosure, "skin" refers to the tissue covering the outer surface of an animal. The term is used in the broadest concept, comprising not only the tissue covering the outer surface such as face, body, etc., but also the scalp and hair.

The composition according to exemplary embodiments of the present disclosure may be a cosmetic composition comprising the active ingredient.

In an exemplary embodiment, the composition may be formulated by comprising a cosmetically or dermatologically acceptable medium or base. It may be prepared into any formulation suitable for topical application, e.g., a solution, a gel, a solid, an anhydrous paste, an oil-in-water emulsion, a suspension, a microemulsion, a microcapsule, a microgranule, an ionic (liposome) or nonionic vesicular dispersant, a cream, a toner, a lotion, a powder, an ointment, a spray or a conceal stick. Also, it may be used in the form of a foam or an aerosol composition further comprising a compressed propellant. The composition may be prepared according to a method commonly employed in the art.

The composition according to exemplary embodiments of the present disclosure may be a food composition comprising the active ingredient.

For example, the composition may be processed into a functional food comprising the active ingredient, such as fermented milk, cheese, yogurt, juice, a probiotic, a health food, etc. and may also be used in the form of various food additives. In an exemplary embodiment, the composition may be a health food composition. In an exemplary embodiment, the health food composition may be formulated as a pill, a capsule, a tablet, a granule, a caramel, a drink, etc. In another exemplary embodiment, it may be processed into such forms as a liquid, a powder, a granule, a tablet, a tea bag, etc. The composition may be administered by various methods such as simple drinking, administration by injection, spraying, squeezing, etc. The composition may comprise other ingredients, etc. that may provide a synergistic effect to a main effect within a range not negatively affecting the main effect of the present disclosure. For example, it may further comprise an additive such as a flavorant, a colorant, a sterilizer, an antioxidant, an antiseptic, a moisturizer, a thickener, a mineral, an emulsifier, a synthetic polymer, etc. for improvement of physical properties. In addition, it may further comprise an auxiliary ingredient such as a water-soluble vitamin, an oil-soluble vitamin, a polypeptide, a polysaccharide, a seaweed extract, etc. These ingredients may be selected and mixed adequately by those skilled in the art depending on the formulation or purpose of use, and the addition amount thereof may be selected within ranges not negatively affecting the purpose and effect of the present disclosure. For example, the addition amount of these ingredients may be 0.0001-99.9 wt % based on the total weight of the composition.

The composition according to exemplary embodiments of the present disclosure may be a pharmaceutical composition comprising the active ingredient. The pharmaceutical composition may further comprise a pharmaceutical adjuvant such as an antiseptic, a stabilizer, a wetting agent, an emulsification accelerator, a salt and/or buffer for adjusting osmotic pressure, etc. and other therapeutically useful materials. In an exemplary embodiment, the pharmaceutical composition may be a composition for oral administration. For example, the composition for oral administration may be a tablet, a pill, a hard or soft capsule, a liquid, a suspension, an emulsion, a syrup, a powder, a dust, a fine granule, a granule, a pellet, etc. These formulations may further comprise, in addition to the active ingredient, a surfactant, a diluent (e.g., lactose, dextrose, sucrose, mannitol, sorbitol, cellulose and glycine) and a lubricant (e.g., silica, talc, stearic acid and its magnesium or calcium salts, and polyethylene glycol). A tablet may further comprise a binder such as magnesium aluminum silicate, starch paste, gelatin, tragacanth, methyl cellulose, sodium carboxymethyl cellulose or polyvinylpyrrolidone. If necessary, the tablet may further comprise other pharmaceutical additives, for example, a disintegrant such as starch, agar, alginic acid or a sodium salt thereof, an adsorbent, a coloring agent, a flavorant, a sweetener, etc. The tablet may be prepared by a common mixing, granulation or coating method.

In an exemplary embodiment, the pharmaceutical composition may be a composition for parenteral administration, and the composition for parenteral administration may be a formulation for rectal, topical, subcutaneous or transdermal administration. For example, the formulation may be an injection, a medicinal drop, an ointment, a lotion, a gel, a cream, a spray, a suspension, an emulsion, a suppository, a patch, etc., although not being limited thereto.

In an exemplary embodiment, the administration amount of the pharmaceutical composition will vary depending on the age, sex and body weight of the subject to be treated, the particular disease or pathological condition to be treated, the severity of the disease or pathological condition, and the discretion of a prescriber. The determination of the administration amount based on these factors is within the level of those skilled in the art. For example, the administration dosage may be in a range from 1 mg/kg/day to 10 g/kg/day, or from 5 mg/kg/day to 100 mg/kg/day. However, the administration dosage does not limit the scope of the present disclosure by any means.

MODE FOR INVENTION

Hereinafter, the present disclosure will be described in detail referring to examples, comparative examples and test examples. However, the following examples are for illustrative purposes only and it will be obvious to those or ordinary skill in the art that the scope of the present disclosure is not limited by the examples, comparative examples and test examples.

All the experimental values given below are averages of at least three repeated experiments and standard deviation (SD) is represented by error bars. p values were calculated by one-way ANOVA and Dunnett's test, and p values smaller than 0.05 were considered statistically significant.

Example 1: Isolation of Ginsenosides

Fractionation 5.5 kg of *Ginseng* seed (seeds of *Panax ginseng*) was finely ground with a mixer to make a powder form, which was extracted with methanol and then fractionated step by step using n-hexane, ethyl acetate, n-butanol, etc. Lipids were mostly removed by n-hexane, and the lipids remaining in the ethyl acetate fraction were suspended in methanol: water (=1:1 (v/v)), stored in a freezer overnight, and then only the supernatant was taken. The lipids were removed once more using a centrifuge. 2.61 g of the ethyl acetate fraction and 114.64 g of the n-butanol fraction thus pre-treated were fractionated through column and high-performance counter-current chromatography (HPCCC) as follows.

Fractionation of n-Butanol Fraction Using Column and HPCCC 114.64 g of the n-butanol fraction was fractionated by MPLC. n-Hexane/ethyl acetate (=10:1→5:1→1:1) and CHCl$_3$/MeOH (=10:1→5:1 (v/v)) were used as solvents and the flow rate was 50 mL/min. A total of 12 subfractions were obtained under the above conditions, and the components contained in each fraction were separated again using HPCCC, high-performance liquid chromatography (HPLC), Sephadex LH-20 column, etc. Subsequently, 16 compounds were identified by investigating their structure using nuclear magnetic resonance (NMR), ultraviolet (UV) spectroscopy and mass spectrometry (MS).

The isolated 16 compounds comprise: ginsenoside Rg1 (Compound 1), ginsenoside Rg2 (Compound 2) and ginsenoside Re (Compound 3), which are protopanaxatriol saponins; ginsenoside Rd (Compound 4), ginsenoside Rb1 (Compound 5) and ginsenoside Rb2 (Compound 6), which are protopanaxadiol saponins; stigma-5-en-3-O-β-D-glucopyranoside (Compound 7), stigma-5,24(28)-dien-3-O-β-D-glucopyranoside (Compound 8) and stigma-5,22-dien-3-O-β-D-glucopyranoside (Compound 9), which are sterol glycosides; (20S,24R)-6-O-β-D-glucopyranosyl(1→2)-β-D-glucopyranoside-dammar-3-one-20,24-epoxy-6a,12b,25-triol (Compound 10), which is a novel ginsenoside compound according to an exemplary embodiment of the present disclosure first isolated from a natural product; phenethyl alcohol β-D-xylopyranosyl(1→6)-β-D-glucopyranoside) (Compound 12) and eugenyl β-gentiobioside (Compound 13), which are phenolic glycosides; isorhamnetin 3-O-β-D-glucopyranoside (Compound 15), which is a flavonoid; and adenosine (Compound 11), uracil (Compound 14) and tryptophan (Compound 16), which are primary metabolites. The isolation process of Compound 10, which is a novel ginsenoside according to an embodiment of the present disclosure, is shown in FIG. 1. The chemical structures of the 16 compounds are shown in FIGS. 2A-2L, and the spectroscopic evidence and chemical structures of the previously known ginsenosides (Compounds 1-6) among the above compounds are additionally shown in FIGS. 3A-3F.

Compound 10 was isolated as a white amorphous powder with the molecular formula $C_{42}H_{70}O_{15}$ based on the sodiated pseudomolecular ion peak at m/z 837.4617 [(M+Na)$^+$ calcd. 837.4612] in the cationic electrospray ionization-quadru-pole-time-of-flight mass spectrometry (ESI-Q-TOF-MS) spectrum. The $^1$H NMR spectrum of Compound 10 comprises 8 methyl resonance peaks [$\delta_H$ 1.86 (3H, s, H-28), 1.69 (3H, s, H-29), 1.47 (3H, s, H-27), 1.25 (6H, s, H-21, 26), 1.10 (3H, s, H-18), 0.81 (3H, s, H-30), 0.75 (3H, s, H-19)]. In addition, two pairs of signals corresponding to anomeric protons and carbon atoms at two sugar residues were detected at $\delta_H$ 6.02 (1H, d, J=7.8, H-2")/$\delta_C$ 104.08 (C-1') and $\delta_H$ 4.91 (1H, d, J=7.7, H-1')/$\delta_C$ 104.32 (C-1"). The $^{13}$C NMR and heteronuclear single quantum correlation (HSQC) spectra revealed 42 carbon signals. Apart from the above two sugar residues, the aglycone of Compound 10 had eight methylenes, four methines, three oxygen-containing methines [$\delta_C$ 79.79 (C-6), 71.40 (0-12) and 86.09 (C-24)], five quaternary carbon atoms, two oxygenated quaternary carbon atoms [$\delta_C$ 87.15 (0-20) and 70.78 (0-25)], eight methyl groups and carbonyl carbon [$\delta_C$ 218.85 (C-3)]. As a result of thorough interpretation of the $^1$H and $^{13}$C NMR data, the aglycone of Compound 10 was found to be superimposed on pseudoginsengenin R1 [(20S,24R)-dammar-3-one-20,24-epoxy-6α,12β,25-triol])]. The absolute configuration of C-20 in Compound 10 was deduced from S to chemical shift of C-21 ($\delta_C$ 27.67), and the 24R configuration was determined by chemical shift of C-24 ($\delta_C$ 86.09) as previously published. Both sugar units were turned out to be β-D-glucopyranosyl residues from the coupling constants of the anomeric protons in the $^1$H NMR spectra and 12 carbon resonances, together with acid hydrolysis data and gas chromatography (GC) analysis results. A glycoside linkage was determined by heteronuclear multiple bond correlation (HMBC) which showed cross peaks at $\delta_H$ 6.02 (H-1")/$\delta_C$ 79.49 (C-2') and $\delta_H$ 4.91 (H-1')/$\delta_C$ 79.79 (C-6), and it was demonstrated that 2-O-(β-D-glucopyranosyl-β-D-glucopyranosyl residues were linked to C-6 of aglycone at pseudoginsengenin R1. Each of the analytical spectra of Compound 10 and the core HBMC correlation are shown in FIGS. 4 to 10.

As a result of the analysis, the chemical structure of Compound 10 was determined as (20S,24R)-6-O-β-D-glucopyranosyl(1→2)-β-D-glucopyranoside-dammar-3-one-20,24-epoxy-6a,12b,25-triol, and the compound was named pseudoginsenoside RT8 (PG-RTs).

Among the ginsenosides isolated from the ginseng seed extract, ginsenoside Rg1 (Compound 1), ginsenoside Rg2 (Compound 2) and ginsenoside Re (Compound 3), which are protopanaxtriol (PPT)-based ginsenosides, comprise three hydroxyl groups in the ginsenoside backbone. Ginsenoside Rd (Compound 4), ginsenoside Rb1 (Compound 5) and ginsenoside Rb2 (Compound 6), which are protopanaxdiol (PPD)-based ginsenosides, comprise two hydroxyl groups in the ginsenoside backbone. On the other hand, Compound 10, which is a ginsenoside newly isolated and identified in the present disclosure, has a PPT-based backbone, but the terminal hydroxyl group of the backbone is a ketone, and there is a structural difference in that the linear chain of the ginsenoside is cyclized into a furan ring.

Compound 10, which was newly isolated and identified in the present disclosure, had a molecular formula of $C_{42}H_{70}O_{15}$. ESI-Q-TOF-MS m/z was 837.4617 $[M+Na]^+$ and the $^1$H- and $^{13}$C-NMR spectra data are given in the following tables.

TABLE 1

| Position | 13C-NMR | 1H-NMR |
|---|---|---|
| 1 | 40.63 | 1.67 (1H, H-1a)$^a$, 1.49 (1H, H-1b)$^a$ |
| 2 | 33.61 | 2.23 (1H, H-2a)$^a$, 1.78 (1H, H-2b)$^a$ |
| 3 | 218.85 | — |
| 4 | 48.58 | — |
| 5 | 58.35 | 2.06 (1H, d, J = 10.6 Hz, H-5) |
| 6 | 79.79 | 4.15 (1H, H-6)$^a$ |
| 7 | 43.47 | 2.57 (1H, H-7a)$^a$, 1.82 (1H, H-7b)$^a$ |
| 8 | 40.47 | — |
| 9 | 49.47 | 1.60 (1H, H-9)$^a$ |
| 10 | 38.82 | — |
| 11 | 33.47 | 2.22 (1H, H-11a)$^a$, 1.32 (1H, H-11b)$^a$ |
| 12 | 71.40 | 3.68 (1H, td, J = 10.6, 4.5 Hz, H-12) |
| 13 | 49.97 | 1.81 (1H, H-13)$^a$ |
| 14 | 52.76 | — |
| 15 | 33.19 | 1.64 (1H, H-15a)$^a$, 1.26 (1H, H-15b)$^a$ |
| 16 | 25.94 | 2.17 (1H, H-16a)$^a$, 1.87 (1H, H-16b)$^a$ |
| 17 | 48.75 | 2.21 (1H, H-17)$^a$ |
| 18 | 16.13 | 1.10 (3H, s, H-18) |
| 19 | 18.48 | 0.75 (3H, s, H-19) |
| 20 | 87.15 | — |
| 21 | 27.67 | 1.25 (3H, s, H-21) |
| 22 | 32.09 | 1.60 (1H, H-22a)$^a$, 1.37 (1H, H-22b)$^a$ |
| 23 | 29.25 | 1.82 (1H, H-23a)$^a$, 1.25 (1H, H-23b)$^a$ |
| 24 | 86.09 | 3.94 (1H, t, J = 7.5 Hz, H-24) |
| 25 | 70.78 | — |
| 26 | 27.43 | 1.25 (3H, s, H-26) |
| 27 | 28.18 | 1.45 (3H, s, H-27) |
| 28 | 32.95 | 1.86 (3H, s, H-28) |
| 29 | 20.42 | 1.69 (3H, s, H-29) |
| 30 | 18.52 | 0.81 (3H, s, H-30) |

$^a$peak was overlapped

TABLE 2

| Position | 13C-NMR | 1H-NMR |
|---|---|---|
| 6-O-Glc | | |
| 1' | 104.08 | 4.91 (1H, d, J = 7.7 Hz, H-1') |
| 2' | 79.49 | 4.48 (1H, m, H-2') |
| 3' | 80.55 | 4.38 (1H, m, H-3') |
| 4' | 73.05 | 4.16 (1H, m, H-4') |
| 5' | 79.94 | 4.15 (1H, m, H-5') |
| 6' | 63.53 | 4.54 (1H, m, H-6'a), 4.32 (1H, m, H-6'b) |
| 2'-O-Glc | | |
| 1" | 104.32 | 6.02 (1H, d, J = 7.8 Hz, H-1") |
| 2" | 76.34 | 4.18 (1H, m, H-2") |
| 3" | 78.64 | 3.99 (1H, m, H-3") |
| 4" | 72.34 | 4.12 (1H, m, H-4") |
| 5" | 79.11 | 4.27 (1H, m, H-5") |
| 6" | 63.93 | 4.54 (1H, m, H-6"a), 4.32 (1H, m, H-6"b) |

Test Example 1: Comparison of Anti-Inflammatory Effect 1

RAW 264.7 macrophages purchased from ATCC were cultured in Dulbecco's modified Eagle's medium (Sigma) supplemented with 10% fetal bovine serum (FBS; HyClone) and 1% penicillin/streptomycin (Sigma) in a 5% $CO_2$ incubator. After pretreating the RAW 264.7 cells with each of the 7 ginsenosides extracted from ginseng seed (GS #01 to GS #06 and GS #10; 10 μM each) for 2 hours, the cells were further treated with 10 ng/mL lipopolysaccharide (LPS; inflammation-induced group, Sigma) for 6 hours. Then, after extracting RNA using a Trizol™ reagent (Thermo Fisher Scientific), cDNA was synthesized using a RevertAid™ first-strand cDNA synthesis kit (Thermo Fisher Scientific). The expression of inflammation-related genes (IL-1β, IL-6 and iNOS) was observed using a CFX96 real-time quantitative PCR (qPCR) system (Bio-Rad). The result is shown in FIGS. 11-13.

In normal state, IL-1β and IL-6 have important homeostatic functions. However, in most inflammatory states, they are produced excessively, causing pathological changes and inducing many inflammatory diseases in the human body. iNOS is one of nitric oxide synthase isoforms and induces cell death and tissue damage by producing high level of NO in inflammatory responses.

Figure 11:
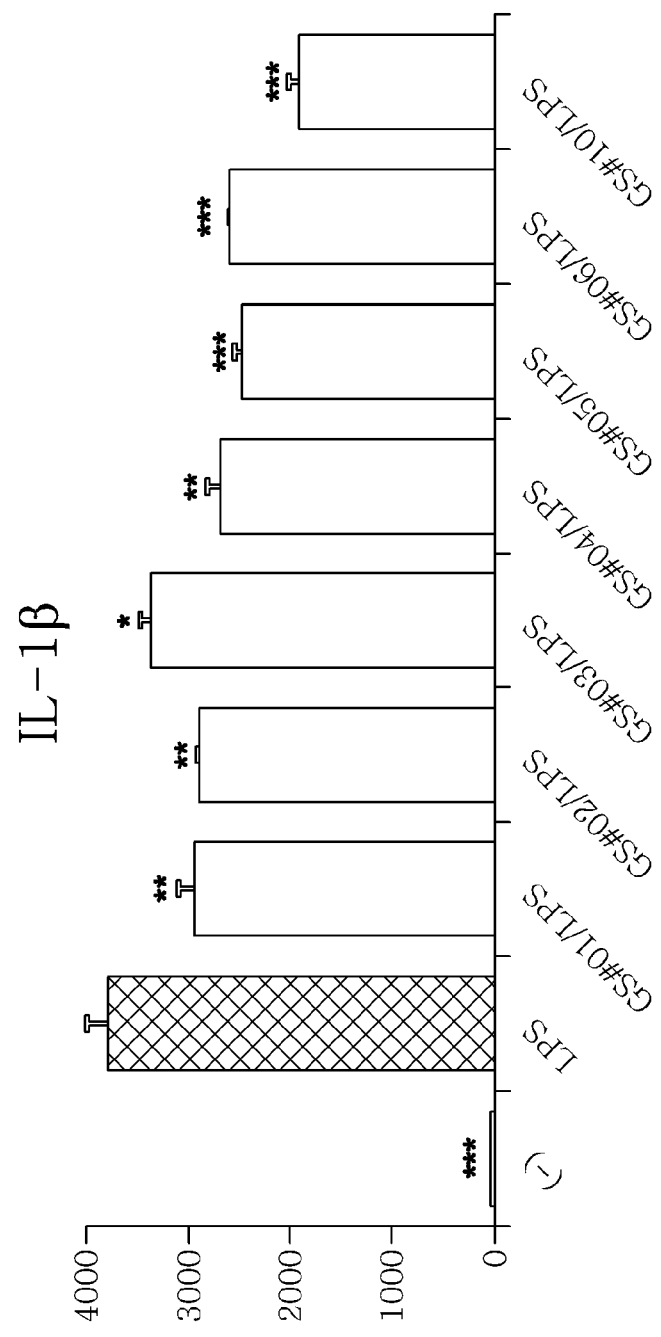
FIG. 11 compares IL-1β expression level for Compounds 1-6 (GS #01-06), corresponding to previously known ginsenosides from among the compounds fractionated from a ginseng seed extract, and Compound 10 (GS #10) corresponding to a novel ginsenoside of the present disclosure (*P<0.001 vs. LPS, P<0.01 vs. LPS, *P<0.05 vs. LPS).
Figure 12:
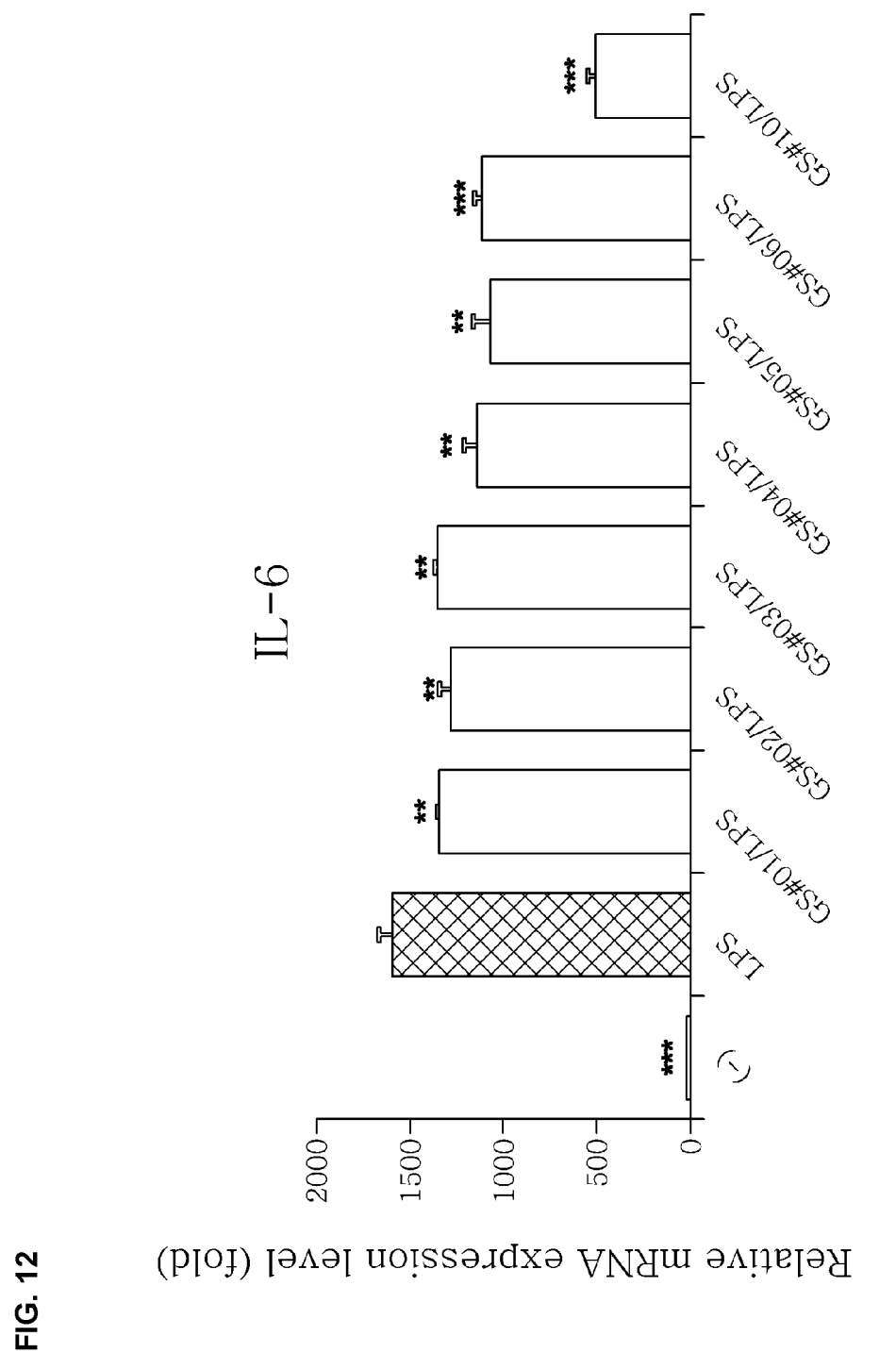
FIG. 12 compares IL-6 expression level for Compounds 1-6 (GS #01-06), corresponding to previously known ginsenosides from among the compounds fractionated from a ginseng seed extract, and Compound 10 (GS #10) corresponding to a novel ginsenoside of the present disclosure (*P<0.001 vs. LPS, P<0.01 vs. LPS, *P<0.05 vs. LPS).
Figure 13:
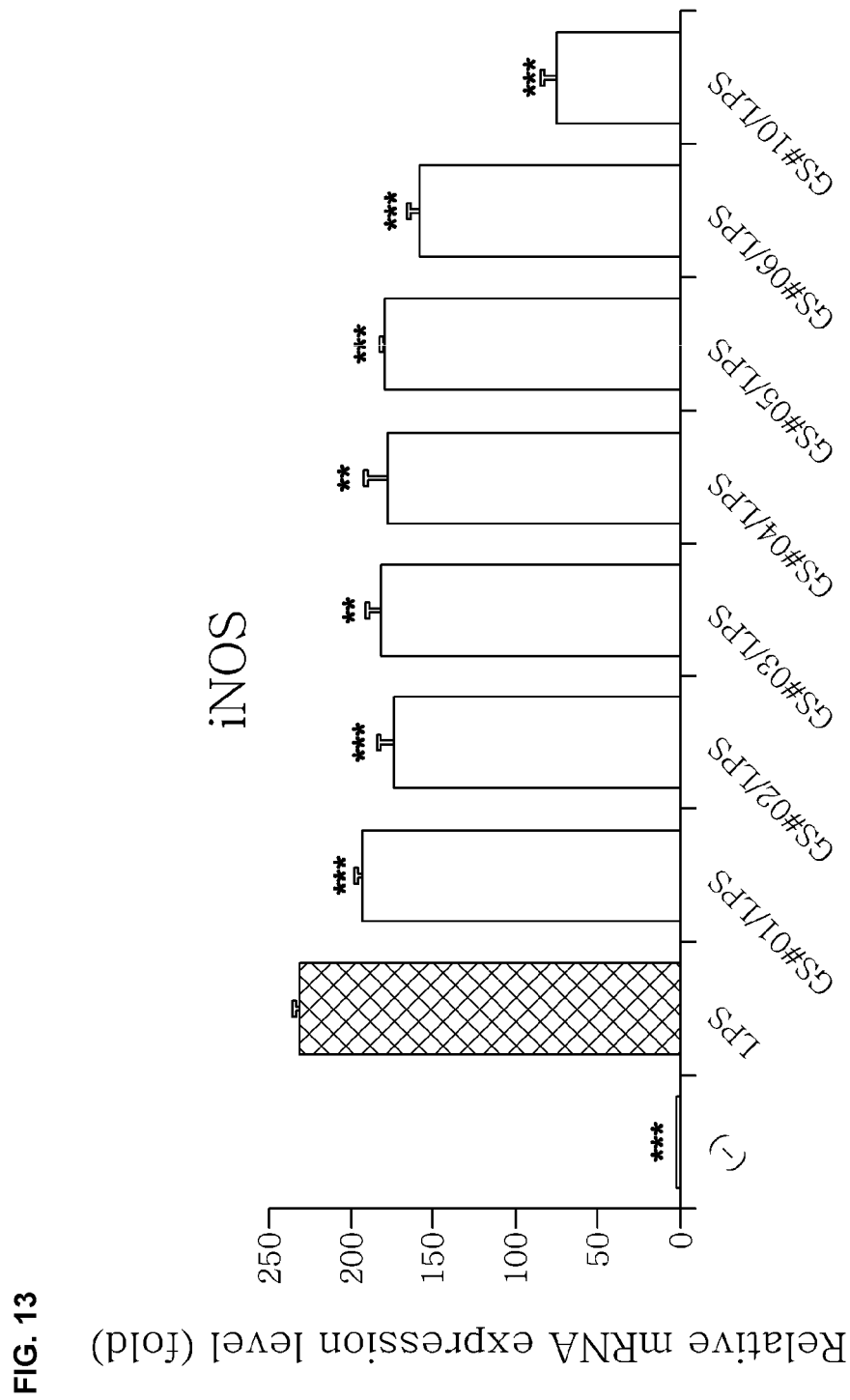
FIG. 13 compares iNOS expression level for Compounds 1-6 (GS #01-06), corresponding to previously known ginsenosides from among the compounds fractionated from a ginseng seed extract, and Compound 10 (GS #10) corresponding to a novel ginsenoside of the present disclosure (*P<0.001 vs. LPS, P<0.01 vs. LPS, *P<0.05 vs. LPS).

As shown in FIGS. 11-13, it can be seen that Compound 10 (GS #10), which is the novel ginsenoside of the present disclosure, can remarkably suppress the expression level of the IL-1β, IL-6 and iNOS genes as compared to Compounds 1-6 (GS #01 to GS #06), which are previously known ginsenosides as comparative examples of the present disclosure, at the same concentration. This is due to the difference in chemical structure and means that the novel ginsenoside of the present disclosure, PG-RT$_8$, has excellent anti-inflammatory effect among the ginseng seed-derived ginsenosides and exhibits stronger anti-inflammatory activity than the previously known steroidal saponins.

Test Example 2: Comparison of Anti-Inflammatory Effect 2

RAW 264.7 macrophages were pretreated with ginsenosides Rg1, Rg3 and Rb1 (purchased from Sigma), which are marker compounds of red ginseng, as comparative examples of the present disclosure or the novel ginsenoside GS #10 (isolated from the ginseng seed extract) as an example of the present disclosure at 1 or 10 μM for 2 hours and then further treated with 10 ng/mL lipopolysaccharide (LPS) for 6 hours to induce inflammation. Then, after extracting RNA and synthesizing cDNA in the same manner as in Test Example 1, the expression of inflammation-related genes was observed by qPCR. The chemical structure of ginsenoside Rg3, which is a comparative example of the present disclosure, is as follows.

Chemical Formula 2

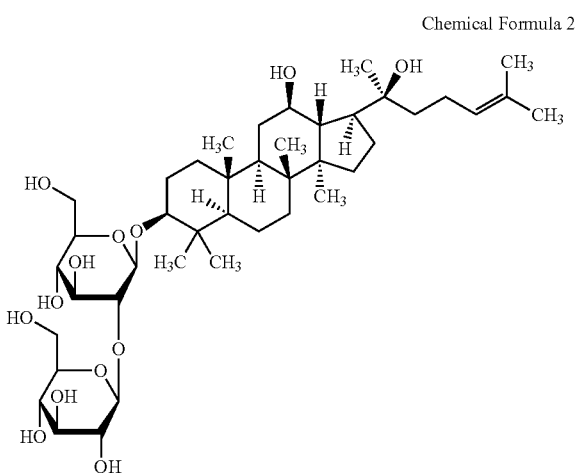

Figure 14:
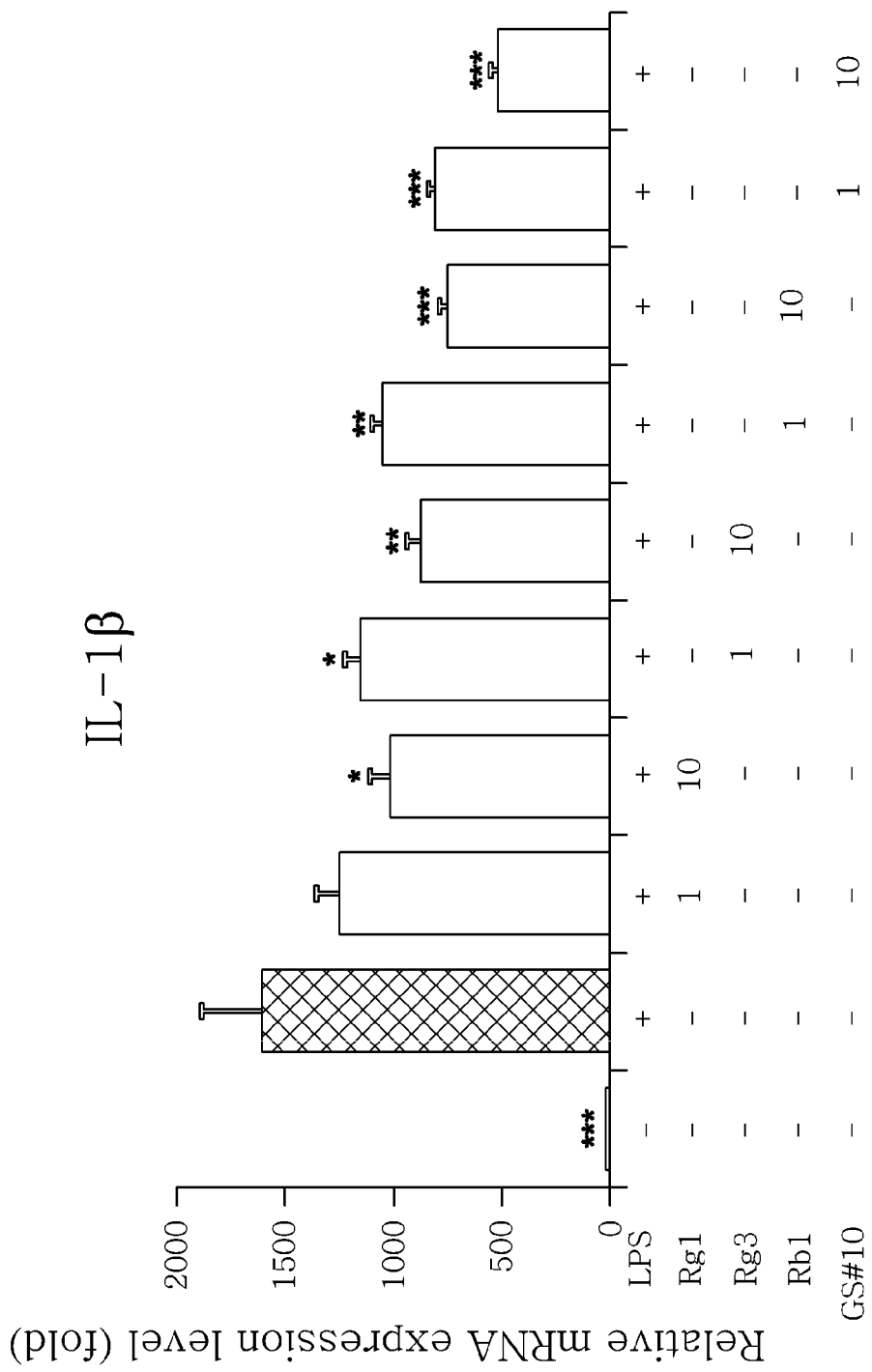
FIG. 14 compares IL-1β expression level for ginsenosides Rg1, Rg3 and Rb1, which are marker compounds of red ginseng, and Compound 10 (GS #10) corresponding to a novel ginsenoside of the present disclosure (*P<0.001 vs. LPS, P<0.01 vs. LPS, *P<0.05 vs. LPS).
Figure 15:
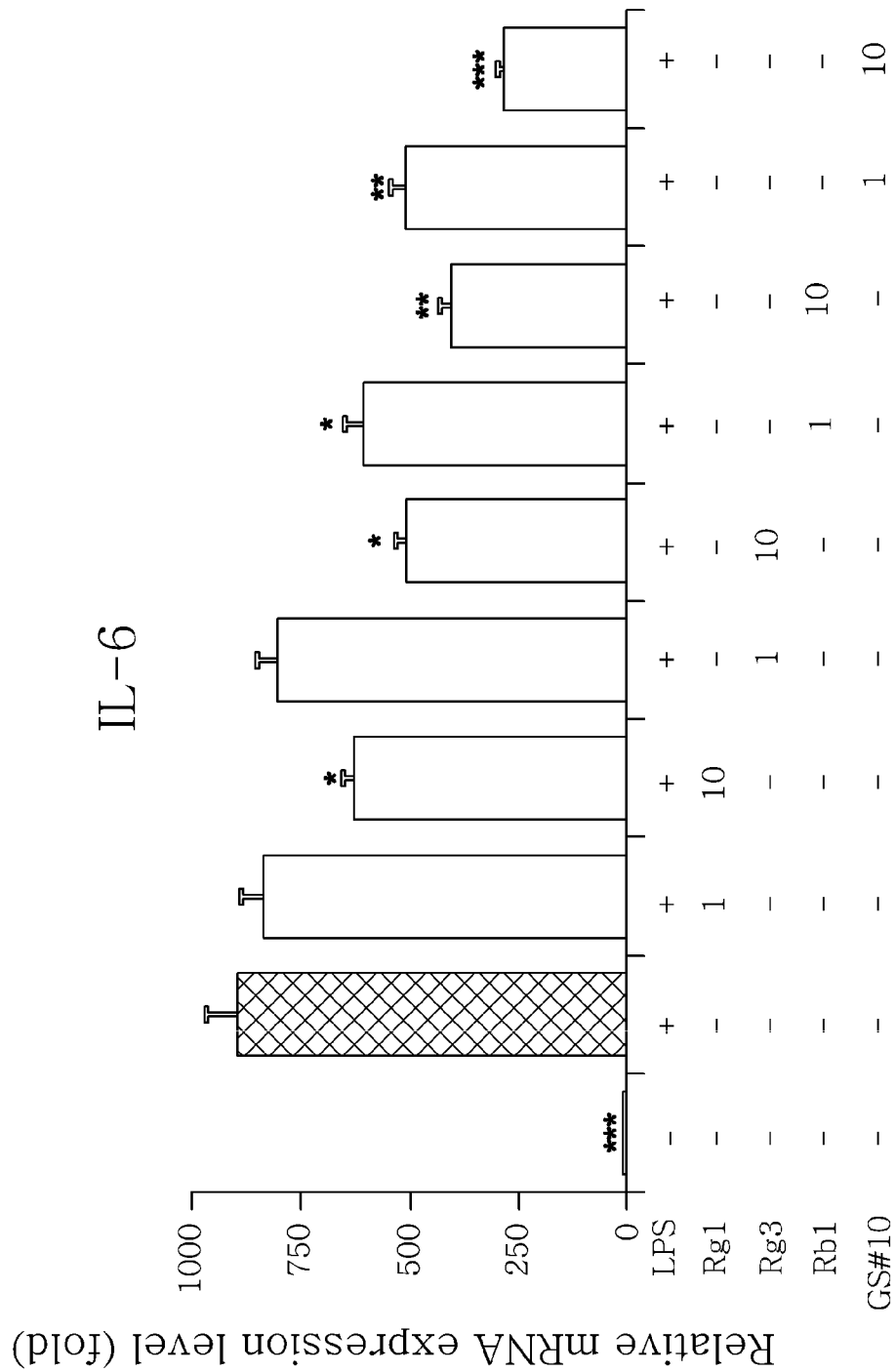
FIG. 15 compares IL-6 expression level for ginsenosides Rg1, Rg3 and Rb1, which are marker compounds of red ginseng, and Compound 10 (GS #10) corresponding to a novel ginsenoside of the present disclosure (*P<0.001 vs. LPS, P<0.01 vs. LPS, *P<0.05 vs. LPS).
Figure 16:
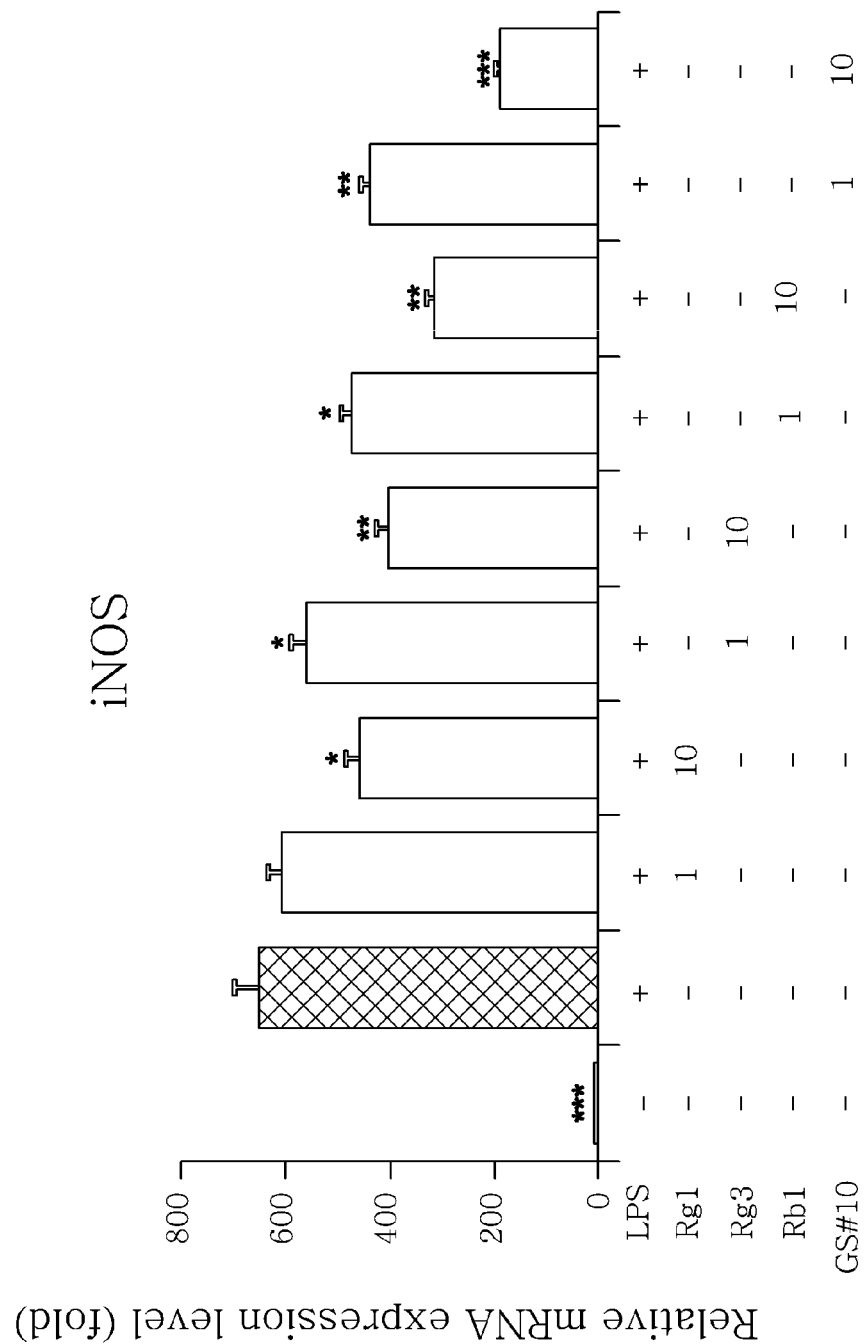
FIG. 16 compares iNOS expression level for ginsenosides Rg1, Rg3 and Rb1, which are marker compounds of red ginseng, and Compound 10 (GS #10) corresponding to a novel ginsenoside of the present disclosure (*P<0.001 vs. LPS, P<0.01 vs. LPS, *P<0.05 vs. LPS).

As seen from FIGS. 14-16, the novel ginsenoside GS #10 of the present disclosure showed remarkably excellent anti-inflammatory effect as compared to the ginsenosides Rg1, Rg3 and Rb1, which are marker compounds of red ginseng. Especially, it was confirmed that the anti-inflammatory effect of GS #10 according to the present disclosure is about 10 times superior to the anti-inflammatory effect of Rg1.

Test Example 3: Secretion of Cytokines

The inhibitory effect on the expression of inflammatory response-related genes by the novel ginsenoside GS #10 of the present disclosure was confirmed in Test Example 2. One step further, it was investigated whether the inhibited expression of the genes actually inhibits the production and secretion inflammation-mediating signaling proteins (inflammatory cytokines).

RAW 264.7 macrophages were used as in Test Example 2. A serum-free medium without comprising FBS was used for the measurement of the amount of cytokines. After pretreating the cells for 2 hours with each ginsenoside at 1 or 10 μM under the same condition as in Test Example 1 and then treating with 10 ng/mL LPS for 6 hours, only the medium was recovered and the secretion of pro-inflammatory cytokines, tumor necrosis factor α (TNF-α), interleukin 1β (IL-1β) and IL-6, was measured using an enzyme-linked immunosorbent assay kit (Abcam).

Figure 17:
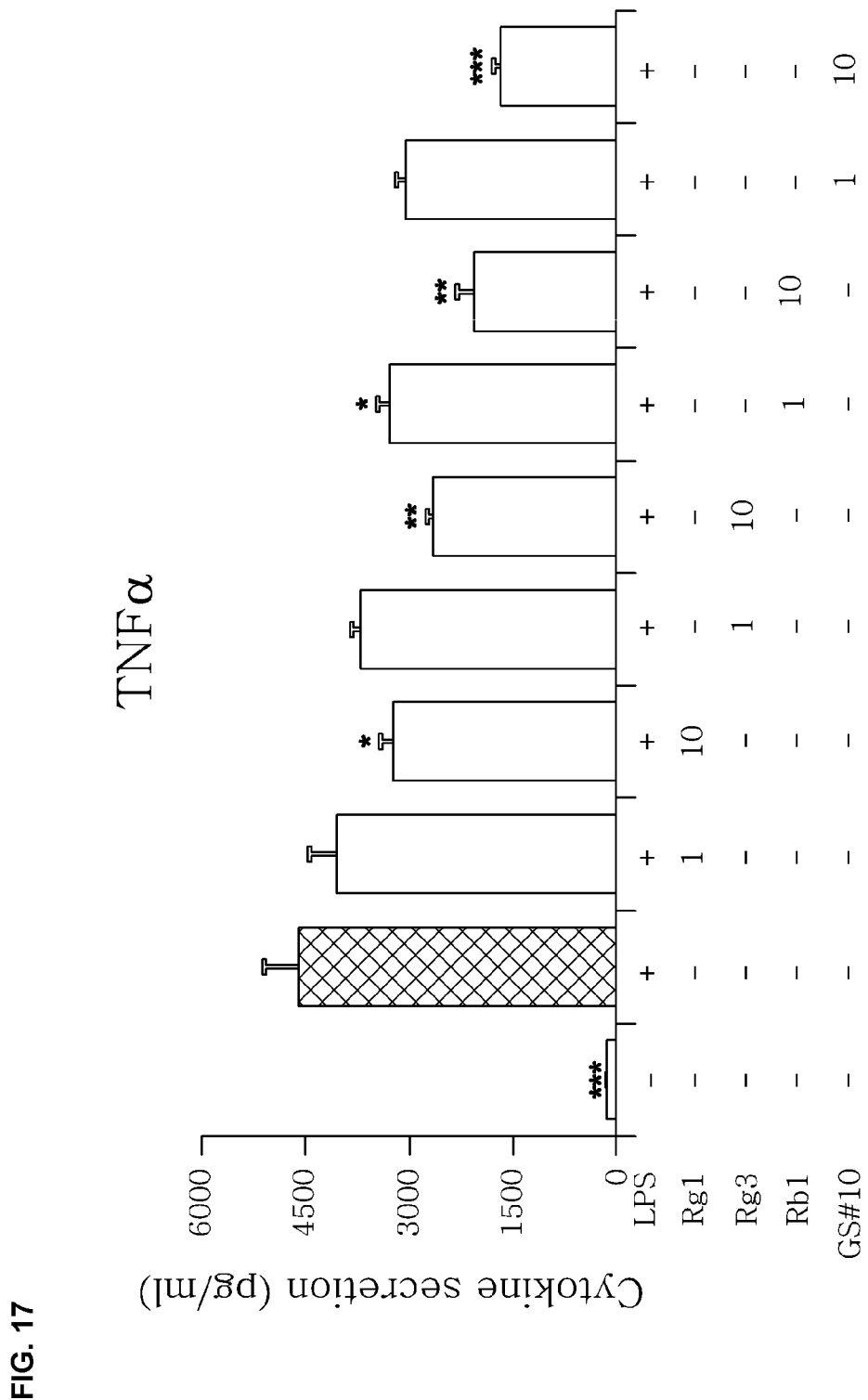
FIG. 17 compares the secretion of the cytokine of TNF-α depending on treatment with ginsenosides Rg1, Rg3 and Rb1, which are marker compounds of red ginseng, and Compound 10 (GS #10) corresponding to a novel ginsenoside of the present disclosure (*P<0.001 vs. LPS, P<0.01 vs. LPS, *P<0.05 vs. LPS).
Figure 18:
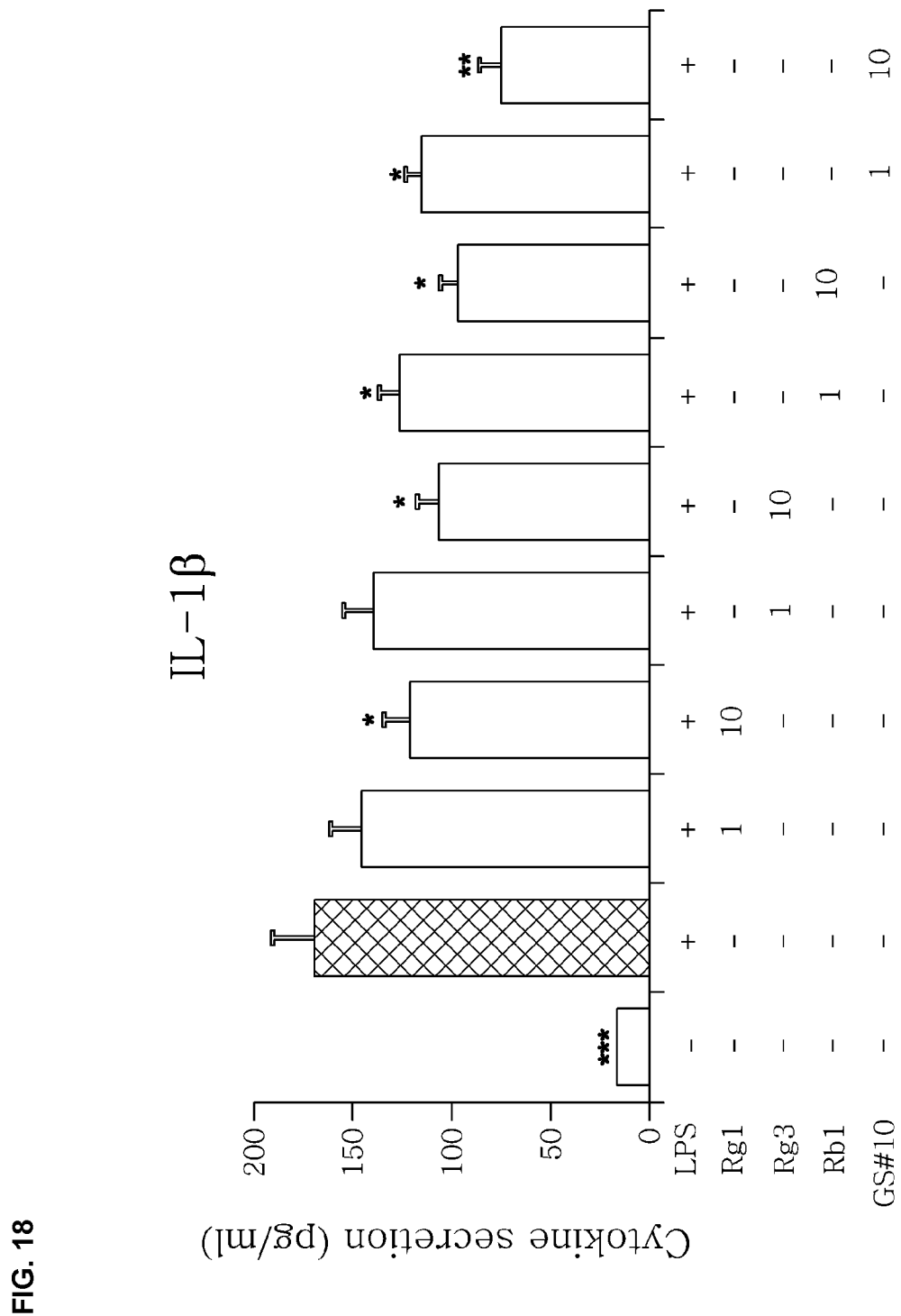
FIG. 18 compares the secretion of the cytokine of IL-18 depending on treatment with ginsenosides Rg1, Rg3 and Rb1, which are marker compounds of red ginseng, and Compound 10 (GS #10) corresponding to a novel ginsenoside of the present disclosure (*P<0.001 vs. LPS, P<0.01 vs. LPS, *P<0.05 vs. LPS).
Figure 19:
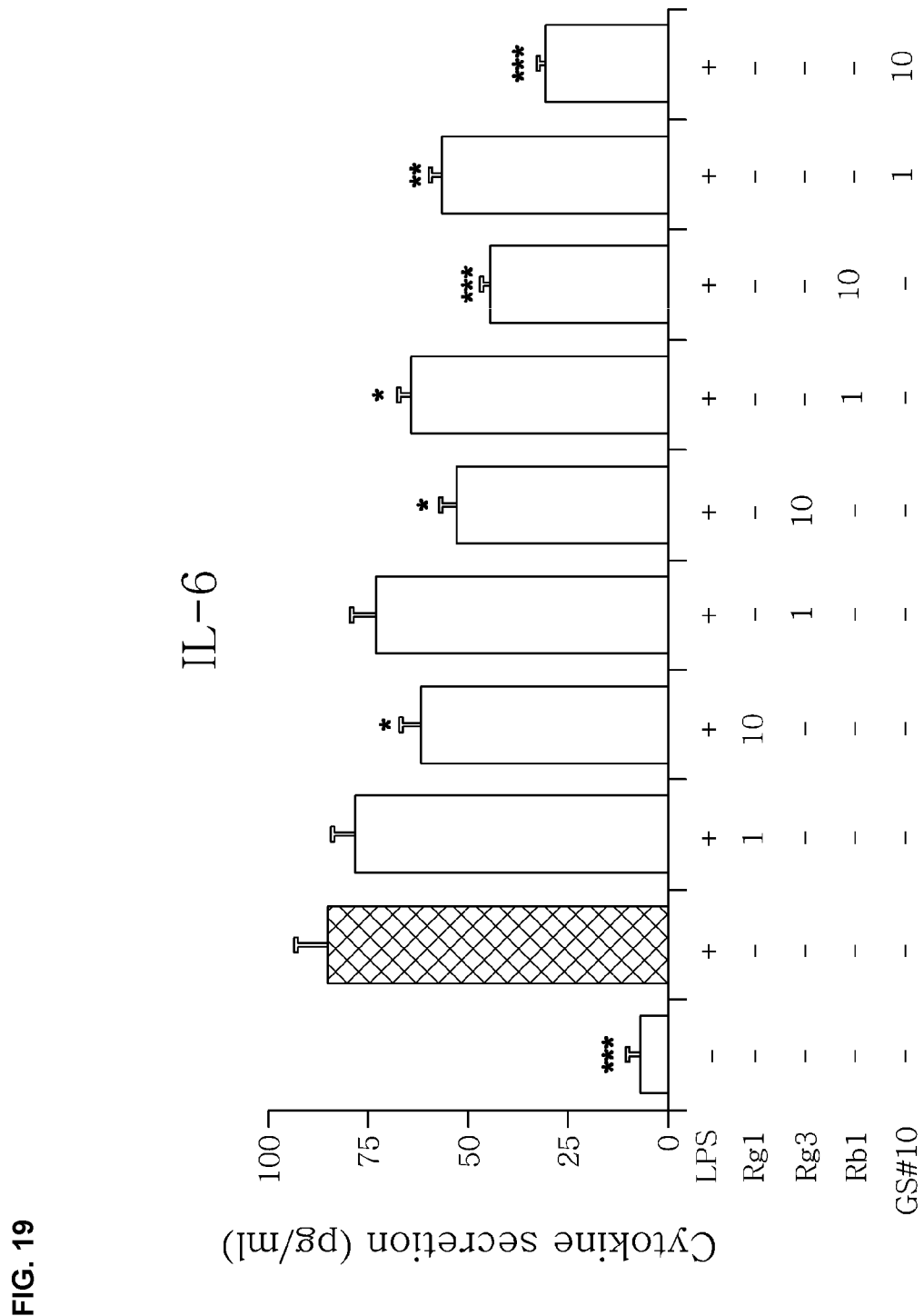
FIG. 19 compares the secretion of the cytokine of IL-6 depending on treatment with ginsenosides Rg1, Rg3 and Rb1, which are marker compounds of red ginseng, and Compound 10 (GS #10) corresponding to a novel ginsenoside of the present disclosure (*P<0.001 vs. LPS, P<0.01 vs. LPS, *P<0.05 vs. LPS).

As shown in FIGS. 17-19, it was confirmed that the secretion of the inflammation-mediating signaling proteins was decreased by the treatment with the ginsenosides Rg1, Rg3 and Rb1, which are marker compounds of red ginseng, as comparative examples of the present disclosure and the novel ginsenoside GS #10 as an example of the present disclosure as the result of Test Example 2. Especially, the treatment with the novel ginsenoside GS #10 as an example of the present disclosure resulted in significant decreased secretion of the inflammation-mediating signaling proteins.

Test Example 4: Inhibition of Nitric Oxide (NO) Production

Pro-inflammatory cytokines mediate the recruitment of activated immune cells to inflammatory tissue, and the effector immune cells build up a cytotoxic condition to get rid of invading pathogens by producing toxic molecules such as NO. Such excessive nitrogen species lead to tissue damage. It was confirmed in Test Example 2 that the novel ginsenoside GS #10 of the present disclosure exhibits superior anti-inflammatory effect as compared to other ginsenosides. In particular, the expression of inducible NO synthase (iNOS) which produces NO, a mediator of inflammatory response, was decreased greatly.

Accordingly, it was investigated whether the novel ginsenoside GS #10 of the present disclosure can inhibit the production of nitric oxide (NO), which is a secondary messenger of inflammatory response.

RAW 264.7 macrophages were treated with 10 μM L-NAME (NO production inhibitor; control group; Sigma), ginsenosides Rg1, Rg3 and Rb1 (purchased from Sigma), which are marker compounds of red ginseng, as comparative examples of the present disclosure or the novel ginsenoside GS #10 (extracted from ginseng seed) as an example of the present disclosure at 1 or 10 μM for 1 hour, and then treated with 10 ng/mL LPS for 1 hour. The amount of NO produced during 1 hour was measured using the Griess reaction. Briefly, after adding 50 μL of sulfanilamide solution to 50 μL of each ginsenoside sample, the mixture was incubated for 10 minutes at room temperature under protection from light. Then, after adding N-(1-napthyl)ethylenediamine solution (50 μL), the mixture was further incubated for 10 minutes at room temperature under protection from light. The anisotropic intensity of NO was measured at a wavelength of 540 nm using a Tecan Infinite® 200 Pro multiplate reader. Sodium nitrite ($NaNO_2$) was used to create a standard curve.

Figure 20:
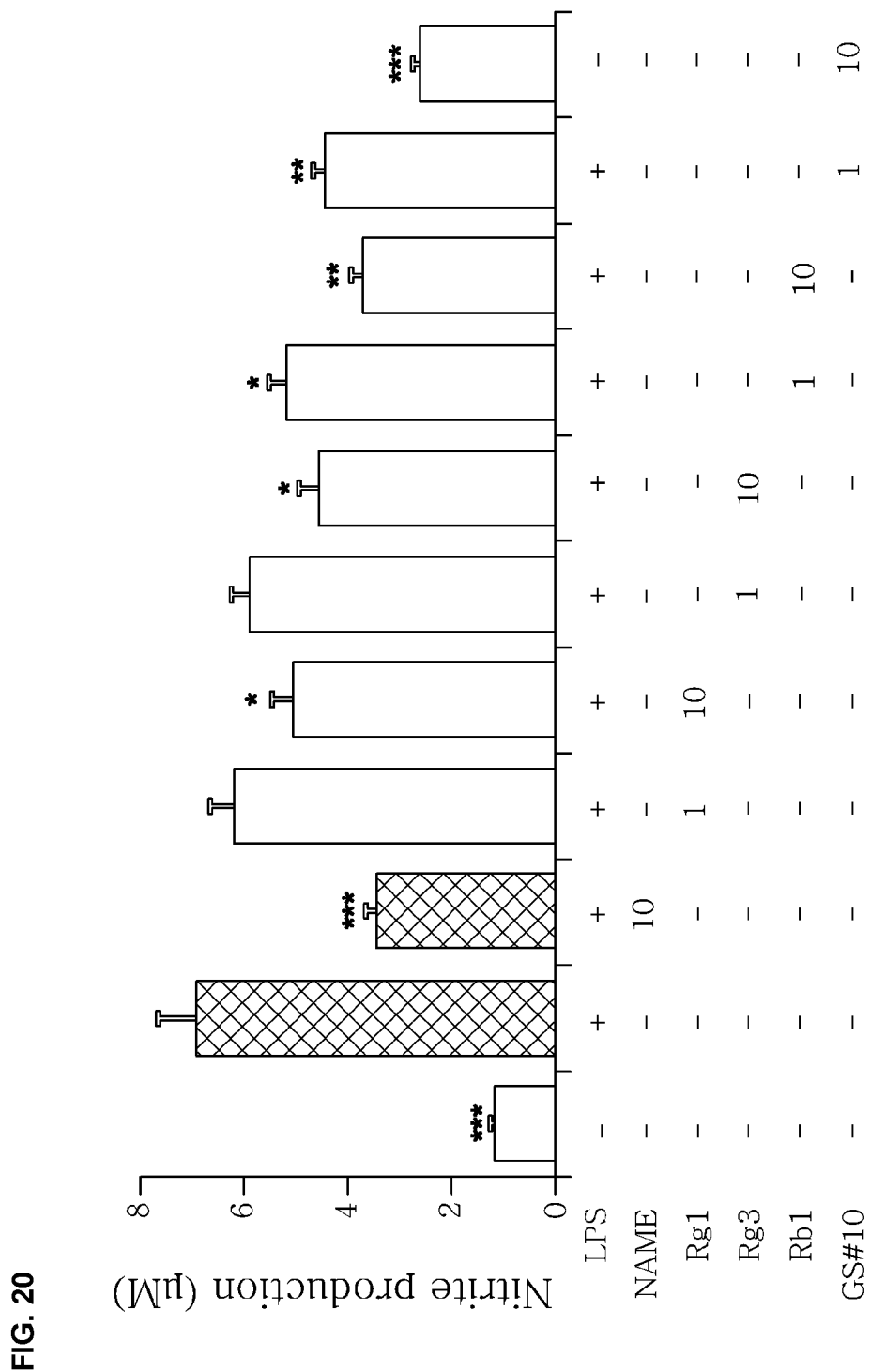
FIG. 20 compares the inhibition of nitric oxide (NO) production depending on treatment with ginsenosides Rg1, Rg3 and Rb1, which are marker compounds of red ginseng, and Compound 10 (GS #10) corresponding to a novel ginsenoside of the present disclosure (*P<0.001 vs. LPS, P<0.01 vs. LPS, *P<0.05 vs. LPS).

As shown in FIG. 20, the production of NO in RAW264.7 macrophages was consistent with the iNOS gene expression pattern observed in Test Example 2. The NO production was decreased as the administration dosage of the novel ginsenoside GS #10 of the present disclosure was increased. In particular, the NO production-inhibiting ability was remarkably superior as compared to the ginsenosides Rg1, Rg3 and Rb1, which are marker compounds of red ginseng, which are comparative examples of the present disclosure.

Test Example 5: Cytotoxicity

In order to exclude the possibility that the ginsenoside might exhibit anti-inflammatory effect through cytotoxic activity, cell growth in the presence of the novel ginsenoside GS #10 according to an exemplary embodiment of the present disclosure was evaluated as follows using CCK (Cell Counting Kit)-8.

After adding 10 μL of CCK-8 reagent to SH-SY5Y cells (Dojindo, MD, USA) on a 96-well plate and maintaining at 37° C. for 2 hours, absorbance was measured at 450 nm.

Cell viability was represented as the percentage (%) of the absolute optical density of each sample with respect to an untreated sample. The concentrations of the novel ginsenoside GS #10 according to an exemplary embodiment of the present disclosure in the medium for culturing the cells were 0.1, 1, 5, 10, 20 and 50 μM.

Figure 21:
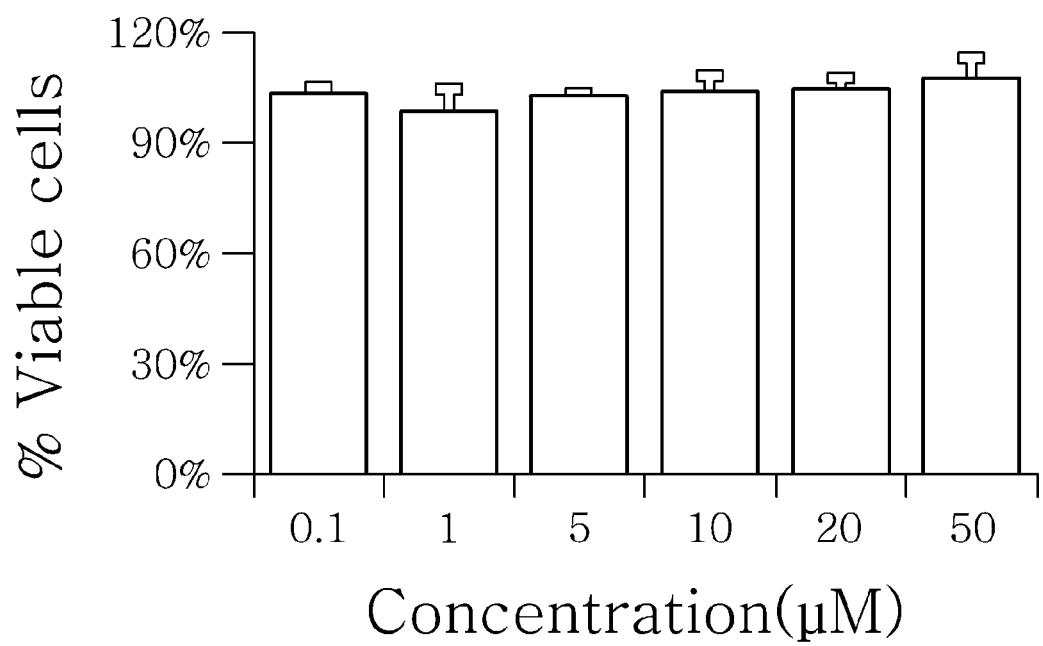
FIG. 21 shows cell survival rate (% viable cells) for Compound 10 (GS #10) corresponding to a novel ginsenoside of the present disclosure (*P<0.001 vs. (−), P<0.01 vs (−), *P<0.05 vs. (−)).

As seen from FIG. 21, the novel ginsenoside GS #10 according to an exemplary embodiment of the present disclosure showed no cytotoxicity up to 50 μM. This result means that the novel ginsenoside according to an exemplary embodiment of the present disclosure can exhibit anti-inflammatory effect without negative effect on cell viability.

The above results suggest that the novel ginsenoside PG-RTs according to an exemplary embodiment of the present disclosure has various powerful anti-inflammatory activities and can be used as an anti-inflammatory agent for pharmaceutical applications.

Hereinafter, formulation examples of the composition according to an exemplary embodiment of the present disclosure are described. However, other various formulations are also possible, and the present disclosure is not limited thereto.

Formulation Example 1: Softening Lotion (Skin Lotion)

A softening lotion was prepared by a common method according to the composition described in the following table.

TABLE 3

| Ingredients | Contents (wt %) |
|---|---|
| PG-RT$_8$ | 0.1 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Antiseptic, colorant and flavorant | Proper amount |
| Purified water | Balance |

Formulation Example 2: Nourishing Lotion (Milk Lotion)

A nourishing lotion was prepared by a common method according to the composition described in the following table.

TABLE 4

| Ingredients | Contents (wt %) |
|---|---|
| PG-RT$_8$ | 0.1 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Antiseptic, colorant and flavorant | Proper amount |
| Purified water | Balance |

Formulation Example 3: Massage Cream

A massage cream was prepared by a common method according to the composition described in the following table.

TABLE 5

| Ingredients | Contents (wt %) |
|---|---|
| PG-RT$_8$ | 0.1 |
| Glycerin | 8.0 |
| Butylene glycol | 4.0 |
| Liquid paraffin | 45.0 |
| β-Glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Antiseptic, colorant and flavorant | Proper amount |
| Purified water | Balance |

Formulation Example 4: Tablet

After mixing 100 mg of ginsenoside PG-RT$_8$, 400 mg of lactose, 400 mg of corn starch and 2 mg of magnesium stearate, a tablet was prepared by tableting the mixture according to a common method.

Formulation Example 5: Capsule

After mixing 100 mg of ginsenoside PG-RT$_8$, 400 mg of lactose, 400 mg of corn starch and 2 mg of magnesium stearate, a capsule was prepared by filling the mixture in a gelatin capsule according to a common method.

Formulation Example 6: Granule

After mixing 50 mg of ginsenoside PG-RT$_8$, 250 mg of anhydrous crystalline glucose and 550 mg starch, the mixture was formed into a granule using a fluidized-bed granule and then filled in a pouch.

Formulation Example 7: Drink

After mixing 50 mg of ginsenoside PG-RT$_8$, 10 g of glucose, 0.6 g of citric acid and 25 g of oligosaccharide syrup and adding 300 mL of purified water, 200 mL of the mixture was filled in a bottle. After the bottle was filled, a drink was prepared by sterilizing the content at 130° C. for 4-5 seconds.

Formulation Example 8: Caramel Formulation

A caramel was prepared by mixing 50 mg of ginsenoside PG-RT$_8$, 1.8 g of corn syrup, 0.5 g of skim milk, 0.5 g of soy lecithin, 0.6 g of butter, 0.4 g of hydrogenated vegetable oil, 1.4 g of sugar, 0.58 g of margarine and 20 mg of table salt.

Formulation Example 9: Health Food

TABLE 6

| Ingredients | Contents |
|---|---|
| PG-RT$_8$ | 100 mg |
| Vitamin mixture | |
| Vitamin A acetate | 70 μg |
| Vitamin E | 1.0 mg |
| Vitamin B$_1$ | 0.13 mg |
| Vitamin B$_2$ | 0.15 mg |
| Vitamin B$_6$ | 0.5 mg |
| Vitamin B$_{12}$ | 0.2 μg |
| Vitamin C | 10 mg |
| Biotin | 10 μg |

TABLE 6-continued

| Ingredients | Contents |
|---|---|
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

Although the above composition of the vitamin and mineral mixtures was presented as an example relatively suitable for health foods, the composition may be varied as desired. According to a common health food preparation method, the above ingredients may be mixed and then prepared into a granule, which may be used to prepare a health food composition according to a common method.

Formulation Example 10: Health Drink

TABLE 7

| Ingredients | Contents |
|---|---|
| PG-RT$_8$ | 10 mg |
| Citric acid | 1000 mg |
| Oligosaccharide | 100 g |
| Plum concentrate | 2 g |
| Taurine | 1 g |
| Purified water | Balance |
| Total volume | 900 mL |

As shown in the above table, a balance of purified water was added to make a total volume of 900 mL, and the above ingredients were mixed according to a common method for preparing a healthy drink, and heated at 85° C. under stirring for about 1 hour. Then, the resulting solution was filtered and collected in a sterilized 2-L container, sterilized, sealed, and then stored in a refrigerator for use in preparation of a healthy drink composition.

Formulation Example 11: Injection

An injection was prepared according to a common method with the composition described in the following table.

TABLE 8

| Ingredients | Contents |
|---|---|
| PG-RT$_8$ | 10-50 mg |
| Sterile distilled water for injection | Proper amount |
| pH control agent | Proper amount |

The present disclosure may provide the following exemplary embodiments.

A first exemplary embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof.

A second exemplary embodiment may provide an anti-inflammatory composition comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof as an active ingredient.

A third exemplary embodiment may provide the composition according to the second exemplary embodiment, wherein the active ingredient has a structure of Chemical Formula 1.

Chemical Formula 1

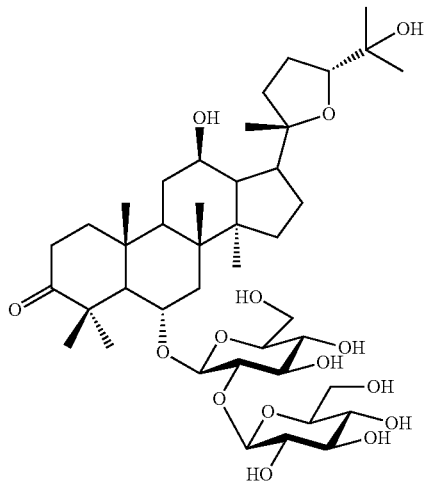

A fourth exemplary embodiment may provide the composition according to the second exemplary embodiment or the third exemplary embodiment, wherein the active ingredient is one extracted from ginseng seed.

A fifth exemplary embodiment may provide the composition according to any of the second to fourth exemplary embodiments, wherein the active ingredient inhibits the expression of one or more gene of interleukin 1β (IL-1β), interleukin 6 (IL-6) and inducible nitric oxide synthase (iNOS).

A sixth exemplary embodiment may provide the composition according to any of the second to fifth exemplary embodiments, wherein the active ingredient inhibits the production or secretion of inflammatory cytokines.

A seventh exemplary embodiment may provide the composition according to any of the second to sixth exemplary embodiments, wherein the active ingredient inhibits the production of nitric oxide.

An eighth exemplary embodiment may provide the composition according to any of the second to seventh exemplary embodiments, wherein the active ingredient is comprised in an amount of 0.0001-99.9 wt % based on the total weight of the composition.

A ninth exemplary embodiment may provide the composition according to any of the second to eighth exemplary embodiment, wherein the composition is a composition for external application to skin.

A tenth exemplary embodiment may provide the composition according to any of the second to ninth exemplary embodiment, wherein the composition is a cosmetic composition.

An eleventh exemplary embodiment may provide the composition according to any of the second to tenth exemplary embodiments, wherein the composition is a food composition.

A twelfth exemplary embodiment may provide the composition according to any of the second to eleventh exemplary embodiments, wherein the composition is a pharmaceutical composition.

The above exemplary embodiments are provided for illustration of the present disclosure, but the scope of the present disclosure is not limited thereby. Accordingly, various modifications, changes and substitutions may be made by those of ordinary skill in the art without departing from the meaning and scope of the present disclosure.

The invention claimed is:

1. A method for treating inflammation comprising administering an effective amount of (20S,24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof to a subject in need thereof.

2. The method according to claim 1, wherein the (20S, 24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof inhibits the expression of one or more gene of interleukin 1β (IL-1β), interleukin 6 (IL-6) and inducible nitric oxide synthase (iNOS).

3. The method according to claim 1, wherein the (20S, 24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof inhibits the production or secretion of inflammatory cytokines.

4. The method according to claim 1, wherein the (20S, 24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof inhibits the production of nitric oxide.

5. The method according to claim 1, wherein the (20S, 24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof is comprised in a composition as an active ingredient, wherein the active ingredient is comprised in an amount of 0.0001-99.9 wt % based on the total weight of the composition.

6. The method according to claim 1, wherein the (20S, 24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof is administered by external application to skin.

7. The method according to claim 1, wherein the (20S, 24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof is comprised in a composition, wherein the composition is a cosmetic composition.

8. The method according to claim 1, wherein the (20S, 24R)-6-O-β-D-glucopyranosyl(1→2)-β-D-glucopyranoside-dammar-3-one-20,24-epoxy-6α,12β,25-triol, a pharmaceutically acceptable salt thereof, a hydrate thereof or a solvate thereof is comprised in a composition, wherein the composition is a food composition.

* * * * *